United States Patent
Nobori et al.

[11] Patent Number: 6,130,346
[45] Date of Patent: Oct. 10, 2000

[54] PROCESS FOR PREPARING AN ORGANIC COMPOUND FROM AN OXIRANE-CONTAINING COMPOUND IN THE PRESENCE OF A TRIS (TRIAMINOPHOSPHORANYLIDENEAMINO) PHOSPHINE OXIDE

[75] Inventors: Tadahito Nobori; Takaomi Hayashi; Isao Hara; Shinji Kiyono; Atsushi Shibahara; Katsuhiko Funaki; Tatsuhiro Urakami; Keisuke Takuma; Usaji Takaki, all of Kanagawa, Japan

[73] Assignee: Mitsui Chemicals, Inc., Japan

[21] Appl. No.: 09/289,989

[22] Filed: Apr. 13, 1999

[30] Foreign Application Priority Data

Apr. 16, 1998 [JP] Japan .................................. 10-106746
Jun. 23, 1998 [JP] Japan .................................. 10-176355

[51] Int. Cl.$^7$ ...................... C07C 319/14; C07C 303/26; C07C 68/00; C07C 67/26; C07C 41/03
[52] U.S. Cl. ......................... 558/51; 558/273; 558/275; 558/276; 560/112; 560/240; 564/14; 568/45; 568/55; 568/648; 568/678; 568/679
[58] Field of Search .................. 558/51, 273, 275, 558/276; 560/112, 240; 568/45, 55, 648, 678, 679

[56] References Cited

FOREIGN PATENT DOCUMENTS 2187454 9/1987 United Kingdom .

OTHER PUBLICATIONS

"Methylation of the phosphoryl group by methyl iodide", G. N. Koidan et al., Journal of General Chemistry of the USSR, vol. 55, No. 7, p. 1453 (Jan. 10, 1996).

"New ring opening reactions of oxiranes with aryl carboxylates", Kazutoshi Funahashi, Bulletin of the Chemical Society of Japan, vol. 52, No. 5, pp. 1488–1492 (1979).

"New catalytic activity of polymer–supported quaternary onium salts. Regioselective addition reaction of oxiranes with active esters catalyzed by insoluble polystyrene–bound quaternary ammonium and phosphonium salts", Tadatomi Nishikubo et al., Journal of Organic Chemistry, vol. 55, No. 8, pp. 2530–2542 (1990).

*Primary Examiner*—Michael G. Ambrose
*Attorney, Agent, or Firm*—Burns, Doane, Swecker & Mathis, L.L.P.

[57] ABSTRACT

A process for preparing an organic compound, comprising conducting an organic reaction in the presence of a phosphine oxide represented by formula (1);

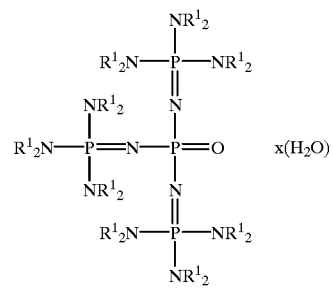

Formula (1)

where $R^1$ is the same or different and each represents a hydrogen or hydrocarbon group with 1 to 10 carbon atoms, and x is the amount of water as a molar ratio which is 0 to 5.0, exhibiting a high catalytic performance especially in an organic reaction involving an alkylene oxide.

17 Claims, No Drawings

PROCESS FOR PREPARING AN ORGANIC COMPOUND FROM AN OXIRANE-CONTAINING COMPOUND IN THE PRESENCE OF A TRIS (TRIAMINOPHOSPHORANYLIDENEAMINO) PHOSPHINE OXIDE

BACKGROUND OF THE INVENTION

1. Field of the Invention

This invention relates to a process for preparing an organic compound as a product by reacting a starting organic compound in the presence of a phosphine oxide represented by formula (1). In particular, this invention relates to an effective process for preparing an oxyalkylene derivative by reacting an epoxy compound with an alcohol, thiol, phenol, thiophenol, carboxylic acid, sulfonic acid, carboxylate, carboxylic anhydride, sulfonate or carbonate. The oxyalkylene derivative is significantly important as, for example, an intermediate for preparation of a herbicide or medicament and a starting material for a polymer.

2. Description of the Prior Art

A phosphine oxide represented by formula (1) has been described only in G. N. Koidan et al., Journal of General Chemistry of the U.S.S.R., vol.55, p.1453 (1985). It describes that tris[tris(N,N-dimethylamido)phosphazo] methoxy-phosphonium iodide may be prepared by reacting methyl iodide with a phosphine oxide represented by formula (1), specifically tris(hexamethyltriamido-phosphazo) phosphate (also named as tris[tris(dimethylamino) phosphoranylideneamino]phosphine oxide where X=O). It, however, does not describe reacting analogous organic compounds except the phosphine oxide in the presence of the phosphine oxide represented by formula (1) or reacting an organic compound except the phosphine oxide with another organic compound except the phosphine oxide. Of course, it or any other document does not describe use of the phosphine oxide represented by formula (1) as a catalyst or polymerization initiator in an organic reaction.

It is known that for example an acid such as boron trifluoride or a base such as tertiary amines and tertiary phosphines may enhance a reaction of an epoxy compound with an alcohol, thiol, phenol, thiophenol, carboxylic acid or sulfonic acid to prepare an oxyalkylene derivative. The conventional acid or base catalysts, however, exhibit inadequate activity.

It is also known that for example tertiary amines, quaternary ammonium salts and quaternary phosphonium salts may enhance a reaction of an epoxy compound with a carboxylate, carboxylic anhydride, sulfonate or carbonate to prepare an oxyalkylene derivative (see K. Funabashi, Bulletin Chemical Society of Japan, vol.52, p.1488 (1979); T. Nishikubo, Yuki Gosei Kyokai Shi, vol.49 (3), p.219 (1991)). However, such a catalyst as the tertiary amines, quaternary ammonium salts and quaternary phosphonium salts also exhibits inadequate activity.

It is, therefore, necessary in either case to increase the amount or concentration of the catalyst or to conduct the reaction under severe conditions, which causes undesirable side reactions and/or degradation of reactants or products.

SUMMARY OF THE INVENTION

An objective of this invention is to provide an effective process for preparing an oxyalkylene derivative with a high yield by using a highly active catalyst for a reaction of an epoxy compound with an alcohol, thiol, phenol, thiophenol, carboxylic acid, sulfonic acid, carboxylate, carboxylic anhydride, sulfonate or carbonate.

We have intensely attempted to achieve the above objective and then have found that a phosphine oxide represented by formula (1) may exhibit a considerably high catalytic activity for a reaction of an epoxy compound with an alcohol, thiol, phenol, thiophenol, carboxylic acid, sulfonic acid, carboxylate, carboxylic anhydride, sulfonate or carbonate to give a desired oxyalkylene derivative with a quite high yield.

This invention provides a process for preparing an organic compound, comprising conducting an organic reaction in the presence of a phosphine oxide represented by formula (1);

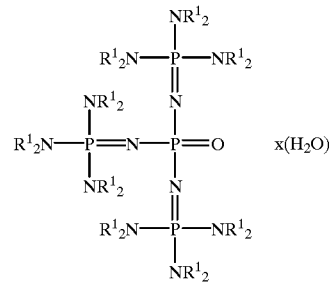

Formula (1)

where $R^1$ is the same or different and each represents a hydrogen or hydrocarbon group with 1 to 10 carbon atoms, and x is the amount of water as a molar ratio which is 0 to 5.0.

Specifically, this invention provides a process for preparing an oxyalkylene derivative, comprising, in the presence of a phosphine oxide represented by formula (1):

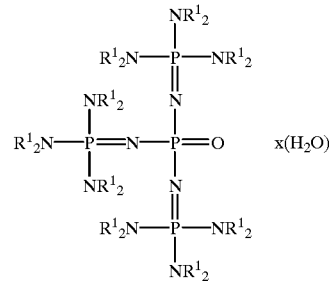

Formula (1)

where $R^1$ is the same or different and each represents a hydrogen or hydrocarbon group with 1 to 10 carbon atoms, and x is the amount of water as a molar ratio which is 0 to 5.0, reacting an epoxy compound with i) an alcohol, thiol, phenol, thiophenol, carboxylic acid or sulfonic acid represented by formula (2):

H—Q  Formula (2)

where H is an active hydrogen and Q is an organic moiety of the alcohol, thiol, phenol, thiophenol, carboxylic acid or sulfonic acid except the active hydrogen;

ii) a carboxylate represented by formula (3), a carboxylic anhydride represented by formula (4) or a sulfonate represented by formula (5):

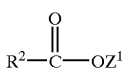

Formula (3)

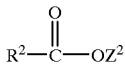

Formula (4)

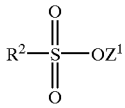

Formula (5)

where in formulas (3), (4) and (5) $R^2$ is hydrogen or an organic group having 1 to 35 carbon atoms; in formulas (3) and (5) $OZ^1$ is an organic moiety of the alcohol or phenol except the active hydrogen; and in formula (4) $OZ^2$ is an organic moiety of the carboxylic acid except the active hydrogen; or iii) a carbonate represented by formula (6)

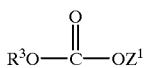

Formula (6)

where $R^3$ is aliphatic hydrocarbon group having 1 to 35 carbon atoms or aromatic hydrocarbon group having 6 to 35 carbon atoms, and $OZ^1$ is as defined above for formula (3) and (5), to form respectively an oxyalkylene derivative having i) a substructure represented by formula (7):

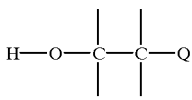

Formula (7)

ii) a substructure represented by formula (8), (9) or (10):

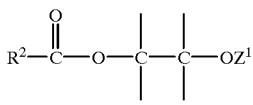

Formula (8)

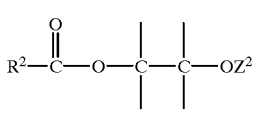

Formula (9)

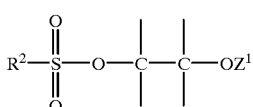

Formula (10)

or iii) a substructure represented by formula (11) and/or a substructure represented by formula (12):

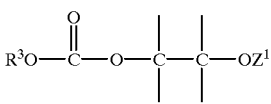

Formula (11)

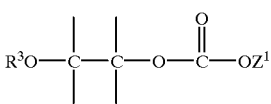

Formula (12)

DESCRIPTION OF THE PREFERRED EMBODIMENTS

Herein, an organic reaction conducted in the presence of a phosphine oxide represented by formula (1) means a reaction of analogous organic compounds except the phosphine oxide (1) or a reaction of a combination of different types of organic compounds except the phosphine oxide represented by formula (1), for preparation of a low molecular weight compound or a polymer. The organic product includes a common low molecular weight reaction product or polymer.

Formula (1) is a limiting structure for a phosphine oxide used in the process of this invention, where phosphorous and oxygen atoms are bound via a double bond. Alternatively, the compound may have a limiting structure where electrons are localized on the oxygen atom to form an anion while the phosphorous has a cationic form, i.e., $p^+$—$O^-$. The positive charge on the phosphorous atom is delocalized over the molecule via conjugated systems. It should be, therefore, noted that the phosphine oxide represented by formula (1) is a resonance hybrid including all the limiting structures.

When the phosphine oxide represented by formula (1) may contain water, an interaction between water and phosphine oxide compound may be any type as long as it does not deteriorate the characteristics of the compound or affect the process of this invention.

In the phosphine oxide represented by formula (1), $R^1$ is the same or different and each represents a hydrogen or hydrocarbon group having 1 to 10 carbon atoms; specifically $R^1$ is selected from hydrogen and aliphatic or aromatic hydrocarbons such as methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (commonly, tert-octyl), nonyl, decyl, phenyl, 4-tolyl, benzyl, 1-phenylethyl and 2-phenylethyl; preferably aliphatic hydrocarbons having 1 to 8 carbon atoms such as methyl, ethyl, n-propyl, isopropyl, tert-butyl, tert-pentyl and 1,1-dimethyl-3,3-dimethylbutyl; more preferably methyl and ethyl.

The phosphine oxides represented by formula (1) may be prepared by the process described in G. N. Koidan et al. Journal of General Chemistry of the U.S.S.R., vol.55, p,1453 (1985) or its modification.

The phosphine oxides represented by formula (1) are generally hygroscopic and thus tends to form a hydrated compound or a hydrate. The amount of water contained in the compound is represented by x which is 0 to 5.0, preferably 0 to 2.0 as a molar ratio to the phosphine oxide. The amount of water is up to several times of that of the catalyst, which may not cause an undesirable effect such as hydrolysis of reactants and/or the oxyalkylene derivative, and the effect may be, if any, trivial and not affect the objective of this invention.

The epoxy compound used in this invention is a 3-membered epoxy-containing organic compound; for example, aliphatic, alicyclic or aromatic epoxy compounds consisting of carbon and hydrogen atoms and an oxygen of the epoxy group such as ethylene oxide, propylene oxide, 1,2-epoxybutane, 2,3-epoxybutane, 1,2-epoxyhexane, 1,2-epoxyoctane, 1,2-epoxydecane, 1,2-epoxydodecane, 1,2-epoxytetradecane, 1,2-epoxyhexadecane, 1,2-epoxyoctadecane, 7,8-epoxy-2-methyloctadecane, 2-vinyloxirane, 2-methyl-2-vinyloxirane, 1,2-epoxy-5-hexene, 1,2-epoxy-7-octene, 1-phenyl-2,3-epoxypropane, 1-(1-naphthyl)-2,3-epoxypropane, 1-cyclohexyl-3,4-epoxybutane, 1,3-butadiene dioxide, 1,2,7,8-diepoxyoctane, cyclopentene oxide, 3-methyl-1,2-cyclopentene oxide, cyclohexene oxide, cyclooctene oxide, α-pinene oxide, 2,3-epoxynorbornane, limonene oxide, cyclododecene oxide, 2,3,5,6-diepoxynorbornane, styrene oxide, 3-methylstyrene oxide, 1,2-epoxybutylbenzene, 1,2-epoxyoctylbenzene, stilbene oxide, 3-vinylstyrene oxide, 1-(1-methyl-1,2-epoxyethyl)-3-(1-methylvinyl)benzene, 1,4-bis(1,2-epoxypropyl)benzene, 1,3-bis(1,2-epoxy-1-methylethyl) benzene and 1,4-bis(1,2-epoxy-1-methylethyl)benzene; halogenated aliphatic, alicyclic or aromatic epoxy compounds such as epifluorohydrin, epichlorohydrin, epibromohydrin, hexafluoropropylene oxide, 1,2-epoxy-4-fluorobutane, 1-(2,3-epoxypropyl)-4-fluorobenzene, 1-(3,4-epoxybutyl)-2-fluorobenzene, 1-(2,3-epoxypropyl)-4-chlorobenzene, 1-(3,4-epoxybutyl)-3-chlorobenzene, 4-fluoro-1,2-cyclohexene oxide, 6-chloro-2,3-epoxybicyclo[2.2.1]heptane, 4-fluorostyrene oxide and 1-(1,2-epoxypropyl)-3-trifluorobenzene; aliphatic, alicyclic or aromatic epoxy compounds having a keto group such as 3-acetyl-1,2-epoxypropane, 4-benzoyl- 1,2-epoxybutane, 4-(4-benzoyl)phenyl-1,2-epoxybutane, 4,4'-bis(3,4-epoxybutyl)benzophenone, 3,4-epoxy-1-cyclohexanone, 2,3-epoxy-5-oxobicyclo[2.2.1]heptane, 3-acetylstyrene oxide and 4-(1,2-epoxypropyl)benzophenone; aliphatic, alicyclic or aromatic epoxy compounds having an ether bond such as glycidyl methyl ether, butyl glycidyl ether, 2-ethylhexyl glycidyl ether, allyl glycidyl ether, ethyl 3,4-epoxybutyl ether, glycidyl phenyl ether, glycidyl 4-tert-butylphenyl ether, glycidyl 4-chlorophenyl ether, glycidyl 4-methoxyphenyl ether, glycidyl 2-phenylphenyl ether, glycidyl 1-naphthyl ether, glycidyl 4-indolyl ether, glycidyl N-methyl-α-quinolon-4-yl ether, ethyleneglycol diglycidyl ether, 1,4-butanediol diglycidyl ether, 1,2-diglycidyloxybenzene, 2,2-bis(4-glycidyloxyphenyl) propane, tris(4-glycidyloxyphenyl)methane, poly (oxypropylene)triol triglycidyl ether, a glycidyl ether of phenol novolac, 1,2-epoxy-4-methoxycyclohexane, 2,3-epoxy-5,6-dimethoxybicyclo[2.2.1]heptane, 4-methoxystyrene oxide and 1-(1,2-epoxybutyl)-2-phenoxybenzene; aliphatic, alicyclic or aromatic epoxy compounds having an ester bond such as glycidyl formate, glycidyl acetate, 2,3-epoxybutyl acetate, glycidyl butyrate, glycidyl benzoate, diglycidyl terephthalate, poly(glycidyl methacrylate), 1,2-epoxy-4-methoxycarbonylcyclohexane, 2,3-epoxy-5-butoxycarbonylbicyclo[2.2.1]heptane, ethyl 4-(1,2-epoxyethyl)benzoate, methyl 3-(1,2-epoxybutyl) benzoate and methyl 3-(1,2-epoxybutyl)-5-phenylbenzoate; aliphatic, alicyclic or aromatic epoxy compounds having an amide bond such as N,N-glycidylmethylacetamide, N,N-ethylglycidylpropionamide, N,N-glycidylmethylbenzamide, N-(4,5-epoxypentyl)-N-methylbenzamide, poly(N-glycidylacrylamide), poly(N,N-glycidylmethylacrylamide), 1,2-epoxy-3-(diphenylcarbamoyl)cyclohexane, 2,3-epoxy-6-(dimethylcarbamoyl)bicyclo[2.2.1]heptane, 2-(dimethylcarbamoyl)styrene oxide and 4-(1,2-epoxybutyl)-4'-(dimethylcarbamoyl)biphenyl; and aliphatic, alicyclic or aromatic epoxy compounds having a cyano group such as 4-cyano-1,2-epoxybutane, 1-(3-cyanophenyl)-2,3-epoxybutane, 5-cyano-2,3-epoxybicyclo[2.2.1]heptane, 2-cyanostyrene oxide and 6-cyano-1-(1,2-epoxy-2-phenylethyl)naphthalene. These compounds may have any other substituent as long as it does not adversely affect the process of this invention.

Preferably it may be selected from aliphatic, alicyclic or aromatic epoxy compounds consisting of carbon and hydrogen atoms and an oxygen of the epoxy group such as ethylene oxide, propylene oxide, 1,2-epoxybutane, 2,3-epoxybutane, 1,2-epoxyhexane, 1,2-epoxyoctane, 1,2-epoxydecane, 1,2-epoxydodecane, 1,2-epoxytetradecane, 1,2-epoxyhexadecane, 1,2-epoxyoctadecane, 7,8-epoxy-2-methyloctadecane, 2-vinyloxirane, 2-methyl-2-vinyloxirane, 1,2-epoxy-5-hexene, 1,2-epoxy-7-octene, 1-phenyl-2,3-epoxypropane, 1-(1-naphthyl)-2,3-epoxypropane, 1-cyclohexyl-3,4-epoxybutane, 1,3-butadiene dioxide, 1,2,7,8-diepoxyoctane, cyclopentene oxide, 3-methyl-1,2-cyclopentene oxide, cyclohexene oxide, cyclooctene oxide, α-pinene oxide, 2,3-epoxynorbornane, limonene oxide, cyclododecene oxide, 2,3,5,6-diepoxynorbornane, styrene oxide, 3-methylstyrene oxide, 1,2-epoxybutylbenzene, 1,2-epoxyoctylbenzene, stilbene oxide, 3-vinylstyrene oxide, 1-(1-methyl-1,2-epoxyethyl)-3-(1-methylvinyl)benzene, 1,4-bis(1,2-epoxypropyl)benzene, 1,3-bis(1,2-epoxy-1-methylethyl) benzene and 1,4-bis(1,2-epoxy-1-methylethyl)benzene; and aliphatic, alicyclic or aromatic epoxy compounds having an ether bond such as glycidyl methyl ether, butyl glycidyl ether, 2-ethylhexyl glycidyl ether, allyl glycidyl ether, ethyl 3,4-epoxybutyl ether, glycidyl phenyl ether, glycidyl 4-tert-butylphenyl ether, glycidyl 4-chlorophenyl ether, glycidyl 4-methoxyphenyl ether, glycidyl 2-phenylphenyl ether, glycidyl 1-naphthyl ether, glycidyl 4-indolyl ether, glycidyl N-methyl-α-quinolon-4-yl ether, ethyleneglycol diglycidyl ether, 1,4-butanediol diglycidyl ether, 1,2-diglycidyloxybenzene, 2,2-bis(4-glycidyloxyphenyl) propane, tris(4-glycidyloxyphenyl)methane, poly (oxypropylene)triol triglycidyl ether, a glycidyl ether of phenol novolac, 1,2-epoxy-4-methoxycyclohexane, 2,3-epoxy-5,6-dimethoxybicyclo[2.2.1]heptane, 4-methoxystyrene oxide and 1-(1,2-epoxybutyl)-2-phenoxybenzene.

More preferably it may be selected from aliphatic epoxy compounds having 2 to 13 carbon atoms consisting of carbon and hydrogen atoms and an oxygen of the epoxy group such as ethylene oxide, propylene oxide, 1,2-epoxybutane, 2,3-epoxybutane, 1,2-epoxyhexane, 1,2-epoxyoctane, 1,2-epoxydecane, 1,2-epoxydodecane, 2-vinyloxirane, 2-methyl-2-vinyloxirane, 1,2-epoxy-5-hexene, 1,2-epoxy-7-octene, 1-phenyl-2,3-epoxypropane, 1-(1-naphthyl)-2,3-epoxypropane, 1-cyclohexyl-3,4-epoxybutane, 1,3-butadiene dioxide and 1,2,7,8-diepoxyoctane; and aliphatic epoxy compounds having 4 to 21 carbon atoms having an ether bond such as glycidyl methyl ether, butyl glycidyl ether, 2-ethylhexyl glycidyl ether, allyl glycidyl ether, ethyl 3,4-epoxybutyl ether, glycidyl phenyl ether, glycidyl 4-tert-butylphenyl ether, glycidyl 4-chlorophenyl ether, glycidyl 4-methoxyphenyl ether, glycidyl 2-phenylphenyl ether, glycidyl 1-naphthyl ether, glycidyl 4-indolyl ether, glycidyl N-methyl-α-quinolon-4-yl ether, ethyleneglycol diglycidyl ether, 1,4-butanediol diglycidyl ether, 1,2-diglycidyloxybenzene and 2,2-bis(4-glycidyloxyphenyl)propane.

In an embodiment of this invention, the epoxy compound is reacted with an alcohol, thiol, phenol, thiophenol, carboxylic acid or sulfonic acid represented by formula (2)

   Formula (2)

where H is an active hydrogen and Q is an organic moiety of the alcohol, thiol, phenol, thiophenol, carboxylic acid or sulfonic acid except the active hydrogen, to prepare an oxyalkylene derivative having a substructure represented by formula (7):

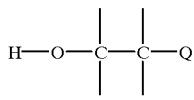   Formula (7)

The alcohol represented by formula (2) may be selected from aliphatic or alicyclic alcohols consisting of carbon and hydrogen atoms and an oxygen atom of the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, docosanol, hexacosanol, triacontanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, β-citronellol, dihydromyrcenol, oleyl alcohol, nerolidol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol, glycerol, poly(vinyl alcohol), cyclobutanol, cyclopentanol, cyclohexanol, 2-methylcyclohexanol, menthol, cycloheptanol, cyclooctanol, cyclododecanol, norborneol, borneol, decahydro-1-naphthol, 1-adamantanol, 2-cyclohexen-1-ol, terpinen-4-ol, carveol, 5-norbonen-2-ol and ergocalciferol; halogenated aliphatic or alicyclic alcohols such as 2-fluoroethanol, 2-chloropropanol, 3-chloro-2,2-dimethylpropanol, 6-chloro-1-hexanol, 2,2,3,3-tetrafluoropropanol, 2-chloro-2-propen-1-ol, 4-chlorobenzyl alcohol, 3-(6-chloro-1-naphthyl)propanol and 2-chlorocyclohexanol; aliphatic or alicyclic alcohols having an ether bond such as 2-methoxyethanol, 1-methoxy-2-propanol, 3-cyclohexyloxy-1-propanol, diethylene glycol monomethyl ether, dipropylene glycol monomethyl ether, diethylene glycol, dipropylene glycol, triethylene glycol, poly(oxypropylene)triol, 2-ethoxybenzyl alcohol, 3-phenoxybenzyl alcohol, 6-methoxy-2-naphthalenethanol, tetrahydro-4H-pyran-4-ol and 1,4-dioxan-2,3-diol; aliphatic or alicyclic alcohols having an ester bond such as 3-acetoxy-1-propanol, 2-(3-methylbenzoyloxy)-1-ethanol, 4-hydroxybutyl methacrylate, 3-acetoxycinnamic alcohol, 2-hydroxyethyl 3-(2-hydroxyethyloxy)benzoate, bis(2-hydroxypropyl)succinate, 3-methoxycarbonylcyclohexanol, 4-vinyloxycarbonylcyclohexanol and bis(2-hydroxyethyl)terephthalate; aliphatic or alicyclic alcohols having an amide bond such as N-(2-hydroxyethyl)acetamide, 3-(dimethylcarbamoyl)-1-propanol, N-(3-hydroxypropyl)acrylamide, N-(4-hydroxycyclohexyl)benzamide and di-N-(2-hydroxyethyl)phthalamide. These compounds may have any other substituent as long as it does not adversely affect the process of this invention.

Preferably it may be selected from aliphatic alcohols consisting of carbon and hydrogen atoms and an oxygen atom of the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, docosanol, hexacosanol, triacontanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, β-citronellol, dihydromyrcenol, oleyl alcohol, nerolidol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol, glycerol and poly(vinyl alcohol); and aliphatic alcohols having an ether bond such as 2-methoxyethanol, 1-methoxy-2-propanol, 3-cyclohexyloxy-1-propanol, diethylene glycol monomethyl ether, dipropylene glycol monomethyl ether, diethylene glycol, dipropylene glycol, triethylene glycol, poly(oxypropylene)triol, 2-ethoxybenzyl alcohol, 3-phenoxybenzyl alcohol and 6-methoxy-2-naphthalenethanol.

More preferably it may be selected from aliphatic alcohols having 1 to 20 carbon atoms consisting of carbon and hydrogen atoms and an oxygen atom of the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol and glycerol.

The thiol represented by formula (2) may be selected from aliphatic or alicyclic thiols consisting of carbon and hydrogen atoms and a sulfur atom of the thiol mercapto group such as methanethiol, ethanethiol, 1-propanethiol, 1-butanethiol, 1-pentanethiol, 1-hexanethiol, 1-heptanethiol, 1-octanethiol, 1-nonanethiol, 1-decanethiol, 1-dodecanethiol, 1-hexadecanethiol, 1-octadecanethiol, 2-methyl-1-propanethiol, 2-methyl-1-butanethiol, 3-methyl-1-butanethiol, 2-propanethiol, 1-methyl-1-propanethiol, 2-methyl-2-propanethiol, 2-methyl-2-butanethiol, tert-dodecanethiol, 1,2-ethanedithiol, 2,3-butanedithiol, 1,9-nonanedithiol, 1,2,3-trimercaptopropane, allyl mercaptan, benzyl mercaptan, phenethyl mercaptan, 3-phenylpropyl mercaptan, triphenylmethyl mercaptan, 1,3-bis(2-mercaptoethyl)benzene, cyclopentyl mercaptan and cyclohexyl mercaptan; halogenated aliphatic or alicyclic thiols such as 2,2,2-trifluoroethanethiol, 3-chloro-1-propanethiol, 2-bromobenzyl mercaptan, 3-chlorophenethyl mercaptan, 3-fluorocyclopentyl mercaptan and 3-chloro-5-methylcyclohexyl mercaptan; aliphatic or alicyclic thiols having an ether bond such as 3-methoxy-1-propanethiol, 3-phenoxy-2-butanethiol, 4-methoxy-2-methylcyclohexyl mercaptan, di-2-mercaptoethyl ether, 1,2,3-tris(3-mercaptopropoxy)propane and 1,3,5-tris(2-mercaptoethoxy)benzene; and aliphatic or alicyclic thiols having an amide bond such as N-(2-mercaptoethyl)acetamide, N,N-dimethyl-3-(mercaptomethyl)benzamide, 4-(N,N-diethylcarbamoyl) cyclohexyl mercaptan and N-(4-mercaptobutyl)acrylamide. These compounds may have any other substituent as long as it does not adversely affect the process of this invention.

Preferably it may be selected from aliphatic thiols consisting of carbon and hydrogen atoms and a sulfur atom of the thiol mercapto group such as methanethiol, ethanethiol, 1-propanethiol, 1-butanethiol, 1-pentanethiol, 1-hexanethiol, 1-heptanethiol, 1-octanethiol, 1-nonanethiol, 1-decanethiol, 1-dodecanethiol, 1-hexadecanethiol, 1-octadecanethiol, 2-methyl-1-propanethiol, 2-methyl-1-butanethiol, 3-methyl-1-butanethiol, 2-propanethiol, 1-methyl-1-propanethiol, 2-methyl-2-propanethiol, 2-methyl-2-butanethiol, tert-dodecanethiol, 1,2-ethanedithiol, 2,3-butanedithiol, 1,9-nonanedithiol, 1,2,3-trimercaptopropane, allyl mercaptan, benzyl mercaptan, phenethyl mercaptan, 3-phenylpropyl mercaptan, triphenylmethyl mercaptan and 1,3-bis(2-mercaptoethyl)benzene; and aliphatic thiols having an ether bond such as 3-methoxy-1-propanethiol, 3-phenoxy-2-butanethiol, di-2-mercaptoethyl ether, 1,2,3-tris(3-mercaptopropoxy)propane and 1,3,5-tris(2-mercaptoethoxy)benzene.

More preferably it may be selected from aliphatic thiols having 1 to 16 carbon atoms consisting of carbon and hydrogen atoms and a sulfur atom of the thiol mercapto group such as methanethiol, ethanethiol, 1-propanethiol, 1-butanethiol, 1-pentanethiol, 1-hexanethiol, 1-heptanethiol, 1-octanethiol, 1-nonanethiol, 1-decanethiol, 1-dodecanethiol, 1-hexadecanethiol, 2-methyl-1-propanethiol, 2-methyl-1-butanethiol, 3-methyl-1-butanethiol, 2-propanethiol, 1-methyl-1-propanethiol, 2-methyl-2-propanethiol, 2-methyl-2-butanethiol, tert-dodecanethiol, 1,2-ethanedithiol, 2,3-butanedithiol, 1,9-nonanedithiol, 1,2,3-trimercaptopropane, allyl mercaptan, benzyl mercaptan, phenethyl mercaptan, 3-phenylpropyl mercaptan, triphenylmethyl mercaptan and 1,3-bis(2-mercaptoethyl)benzene.

The phenol represented by formula (2) may be selected from phenols consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tris(4-hydroxyphenyl)methane, phenol novolak, poly(4-hydroxystyrene) and poly(4-hydroxy-α-methylstyrene); halogenated phenols such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol; phenols having an ether bond such as 2-ethoxyphenol, 4-(phenoxymethyl)phenol, 3,4,5-trimethoxyphenol, 7-methoxy-2-naphthol, 4-benzyloxy-3-methoxyphenol and 3,3'-(ethylenedioxy)diphenol; phenols having a keto group such as 3-hydroxyacetophenone, 2-(2-oxopropyl)phenol, 4-hydroxybenzophenone, 1-hydroxy-2-acenaphthone, 4,4'-dihydroxybenzophenone, 2,6-dihydroxyacetophenone and phloretin; phenols having an ester bond such as 4-acetoxymethylphenol, methyl salicylate, 4-hydroxybenzyl acrylate, ethyl 4-hydroxy-3-methoxycinnamate, 2-methoxycarbonyl-6-methyl-3-naphthol, 1,2-bis(4-hydroxybenzoyloxy)ethane and ethyl 3,4,5-trihydroxybenzoate; and phenols having an amide bond such as 4-acetaminophenol, 3-(N,N-dimethylcarbamoyl)phenol, 4-(N,N-dimethylcarbamoyl)-3-methylphenol, N-(3-hydroxy-5-methyl)phenylacrylamide, N-(5-hydroxy-8-methyl-2-naphthyl)methacrylamide, N-(4-hydroxybenzyl)benzamide and N,N'-bis(4-hydroxyphenyl)-5-methyl-1,3-benzenedicarboxamide. These compounds may have any other substituent as long as it does not adversely affect the process of this invention.

Preferably it may be selected from phenols consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tris(4-hydroxyphenyl)methane, phenol novolak, poly(4-hydroxystyrene) and poly(4-hydroxy-α-methylstyrene); halogenated phenols such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol; and phenols having an ether bond such as 2-ethoxyphenol, 4-(phenoxymethyl)phenol, 3,4,5-trimethoxyphenol, 7-methoxy-2-naphthol, 4-benzyloxy-3-methoxyphenol and 3,3'-(ethylenedioxy) diphenol.

More preferably it may be selected from phenols having 6 to 27 carbon atoms consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4- hydroxyphenyl)-1,1,3-trimethyl-2,3-dihydroindene, 5-hydroxy-3-(4-hydroxyphenyl)-2,6-dimethyl-3-hexene and tris(4-hydroxyphenyl)methane; halogenated phenols having 6 to 15 carbon atoms such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl) propane, 2,2-bis(4-hydroxyphenyl)-1,1,1,2,2,2-hexafluoropropane and octafluoro-4,4'-biphenol.

The thiophenol represented by formula (2) may be selected from thiophenols consisting of carbon and hydrogen atoms and a sulfur atom of the thiophenol mercapto group such as thiophenol, o-thiocresol, m-thiocresol, p-thiocresol, 2-ethylthiophenol, 2-isopropylthiophenol, 2,6-dimethylthiophenol, 3,4-diethylthiophenol, 2,4-dimethylthiophenol, 4-mercaptobiphenyl, 3-methyl-2-naphthalenethiol, 5-phenyl-1,2-benzenedithiol, 5-butyl-1,3-benzenedithiol, 4,4'-dimercaptobiphenyl, 1,2,6-naphthalenetrithiol and anthracene-1-thiol; halogenated thiophenols such as 2-chlorothiophenol, 2-bromothiophenol, 3-chlorothiophenol, 3-bromothiophenol, 4-fluorothiophenol, 4-chlorothiophenol, 4-bromothiophenol, 2,6-dichlorothiophenol, 2,5-dichlorothiophenol, 3,4-dichlorothiophenol, 4-chloro-1,3-benzenedithiol and 7-bromo-1,2,6-naphthalenetrithiol; and thiophenols having an ether bond such as 2-methoxythiophenol, 3-(2-butoxypropyl)thiophenol, 3-mercapto-4'-ethoxybiphenyl, 6-phenoxy-1-naphthalenethiol, 1,2-bis(4-mercaptophenoxy) ethane and 8-methoxy-2,5-naphthalenedithiol. These compounds may have any other substituent as long as it does not adversely affect the process of this invention.

Preferably it may be selected from thiophenols consisting of carbon and hydrogen atoms and a sulfur atom of the thiophenol mercapto group such as thiophenol, o-thiocresol, m-thiocresol, p-thiocresol, 2-ethylthiophenol, 2-isopropylthiophenol, 2,6-dimethylthiophenol, 3,4-diethylthiophenol, 2,4-dimethylthiophenol, 4-mercaptobiphenyl, 3-methyl-2-naphthalenethiol, 5-phenyl-1,2-benzenedithiol, 5-butyl-1,3-benzenedithiol, 4,4'-dimercaptobiphenyl, 1,2,6-naphthalenetrithiol and anthracene-1-thiol.

More preferably it may be selected from thiophenols having 6 to 12 carbon atoms consisting of carbon and hydrogen atoms and a sulfur atom of the thiophenol mercapto group such as thiophenol, o-thiocresol, m-thiocresol, p-thiocresol, 2-ethylthiophenol, 2-isopropylthiophenol, 2,6-dimethylthiophenol, 3,4-diethylthiophenol, 2,4-dimethylthiophenol, 4-mercaptobiphenyl, 3-methyl-2-naphthalenethiol, 5-phenyl-1,2-benzenedithiol, 5-butyl-1,3-benzenedithiol, 4,4'-dimercaptobiphenyl and 1,2,6-naphthalenetrithiol.

The carboxylic acid represented by formula (2) may be selected from aliphatic, alicyclic or aromatic carboxylic acids consisting of carbon and hydrogen atoms and an oxygen atom of the carboxyl group such as formic acid, acetic acid, propionic acid, butyric acid, isobutyric acid, acrylic acid, methacrylic acid, lauric acid, stearic acid, oleic acid, phenylacetic acid, cyclohexane carboxylic acid, benzoic acid, p-methylbenzoic acid, 2-naphthalene carboxylic acid, 2-norbornane carboxylic acid, 2-norbornene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid, poly(methacrylic acid) and pyromellitic acid; halogenated aliphatic, alicyclic or aromatic carboxylic acids such as 4-chlorobutyric acid, 5-fluoro-2-hexanoic acid, pentafluorophenylacetic acid, 4-chlorobenzoic acid, 3-bromocyclohexane carboxylic acid, 5-chloro-2-bicyclo [2.2.1]hexane carboxylic acid and 6-iodo-1-naphthalene carboxylic acid; aliphatic, alicyclic or aromatic carboxylic acids having an ether bond such as methoxyacetic acid, 4-(4-methylphenoxy)butyric acid, 3-phenoxyphenylacetic acid, 2,2'-ethylenedioxy-diacetic acid, 3-benzyloxycyclohexane carboxylic acid, 5,6-dimethoxy-2-bicyclo[2.2.1]hexane carboxylic acid, 3-phenoxycinnamic acid, 5-methoxyisophthalic acid and 4,4'-ethylenedioxybenzoic acid; aliphatic, alicyclic and aromatic carboxylic acids having an ester bond such as 4-acetoxybutyric acid, monoisopropyl succinate, monomethyl fumarate, monoethyl 1,3-cyclohexane dicarboxylate, monohexyl 2,6-norbornane dicarboxylate, 4-hydroxycarbonylbenzyl acrylate, cyclohexyl 5-methyl-1, 3-benzene dicarboxylate, poly(lactic acid), poly(ε-caprolactone) and 1,2-bis(4-hydroxycarbonylbenzoyloxy) ethane; and aliphatic, alicyclic or aromatic carboxylic acids having an amide bond such as N-acetylalanine, 3-(N,N-dimethylcarbamoyl)propionic acid, N-methacryloylphenylglycine, N-(4-hydroxycyclohexyl) benzamide, 5-(N,N-diethylcarbamoyl)-1-naphthalene carboxylic acid and N,N'-(4-hydroxyphenyl)terephthalamide. These compounds may have any other substituent as long as it does not adversely affect the process of this invention.

Preferably it may be selected from aliphatic or aromatic carboxylic acids consisting of carbon and hydrogen atoms and an oxygen atom of the carboxyl group such as formic acid, acetic acid, propionic acid, butyric acid, isobutyric acid, acrylic acid, methacrylic acid, lauric acid, stearic acid, oleic acid, phenylacetic acid, benzoic acid, p-methylbenzoic acid, 2-naphthalene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid, poly (methacrylic acid) and pyromellitic acid.

More preferably it may be selected from aliphatic carboxylic acids having 1 to 12 carbon atoms and aromatic carboxylic acids having 7 to 12 carbon atoms consisting of carbon and hydrogen atoms and an oxygen atom of the carboxyl group such as formic acid, acetic acid, propionic acid, butyric acid, isobutyric acid, acrylic acid, methacrylic acid, lauric acid, phenylacetic acid, benzoic acid, p-methylbenzoic acid, 2-naphthalene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid and pyromellitic acid.

The sulfonic acid represented by formula (2) may be selected from aliphatic, alicyclic or aromatic sulfonic acids consisting of carbon and hydrogen atoms, a sulfur atom of the sulfonic acid group and an oxygen atom of the sulfonic acid group such as methanesulfonic acid, ethanesulfonic acid, 2-butanesulfonic acid, 1-octanesulfonic acid, 1-hexadecane sulfonic acid, 1,2-ethanedisulfonic acid, 1,4-butanedisulfonic acid, cyclopentanesulfonic acid, 1,3-cyclohexanedisulfonic acid, octahydro-4,4'-biphenyldisulfonic acid, benzenesulfonic acid, p-toluenesulfonic acid, 2,4,6-trimethylbenzenesulfonic acid, 4-n-octylbenzenesulfonic acid, 5-methyl-2-naphthalenesulfonic acid, 8-t-butyl-1,5-naphthalenedisulfonic acid, 5-phenyl-1,3-benzenedisulfonic acid, 4,4'-biphenyldisulfonic acid and 1,1'-bi-2,2'-naphthalenedisulfonic acid; halogenated aliphatic, alicyclic or aromatic sulfonic acids such as 2-chloroethanesulfonic acid, 6-bromo-2-hexanesulfonic acid, 4-chlorobenzenesulfonic acid, pentafluorobenzenesulfonic acid, 3-iodobenzylsulfonic acid and 4-fluorobenzenesulfonic acid; aliphatic, alicyclic or aromatic sulfonic acids having an ether bond such as 2-phenoxyethanesulfonic acid, 3-methoxy-2-butanesulfonic acid, 3-(4-ethoxyphenyl)propanesulfonic acid, 3-methoxycyclohexanesulfonic acid, 4-methoxy-1-octahydronaphthalenesulfonic acid, 4-methoxybenzenesulfonic acid, 4-benzyloxy-1-naphthalenesulfonic acid and 9,10-diethoxy-2-anthracenesulfonic acid; aliphatic, alicyclic or aromatic sulfonic acids having a keto group such as 1-benzoyl-4-methyl-3-pentanesulfonic acid, 4-acetylcyclohexanesulfonic acid, 10-camphorsulfonic acid, 4-acetylbenzenesulfonic acid and anthraquinone-1,5-disulfonic acid; aliphatic, alicyclic or aromatic sulfonic acids having an ester bond such as 3-sulfopropyl acrylate, 3-sulfocyclopentyl methacrylate, 3-methoxycarbonylbenzenesulfonic acid, 4-phenoxycarbonylmethylbenzenesulfonic acid and 6-butoxycarbonyl-1-naphthalenesulfonic acid; and aliphatic, alicyclic or aromatic sulfonic acids having an amide bond such as 3-benzamide-1-propanesulfonic acid, 2-acrylamide-2-methyl-1-propanesulfonic acid, 4-methacrylamidecyclohexanesulfonic acid, 4-acetamidebenzenesulfonic acid, 3-acrylamide-benzenesulfonic acid, 4-(N,N-dimethylcarbamoyl)benzenesulfonic acid and 5-benzamide-2-naphthalenesulfonic acid. These compounds may have any other substituent as long as it does not adversely affect the process of this invention.

Preferably it may be selected from aliphatic or aromatic sulfonic acids consisting of carbon and hydrogen atoms, a sulfur atom of the sulfonic acid group and an oxygen atom of the sulfonic group such as methanesulfonic acid, ethanesulfonic acid, 2-butanesulfonic acid, 1-octanesulfonic acid, 1-hexadecane sulfonic acid, 1,2-ethanedisulfonic acid, 1,4-butanedisulfonic acid, benzenesulfonic acid, p-toluenesulfonic acid, 2,4,6-trimethylbenzenesulfonic acid, 4-n-octylbenzenesulfonic acid, 5-methyl-2-naphthalenesulfonic acid, 8-t-butyl-1,5-naphthalenedisulfonic acid, 5-phenyl-1,3-benzenedisulfonic acid, 4,4'-biphenyldisulfonic acid and 1,1'-bi-2,2'-naphthalenedisulfonic acid.

More preferably it may be selected from aliphatic sulfonic acids having 1 to 16 carbon atoms and aromatic sulfonic acids having 6 to 16 carbon atoms consisting of carbon and hydrogen atoms, a sulfur atom of the sulfonic group and an oxygen atom in the sulfonic group such as methanesulfonic acid, ethanesulfonic acid, 2-butanesulfonic acid, 1-octanesulfonic acid, 1-hexadecane sulfonic acid, 1,2-ethanedisulfonic acid, 1,4-butanedisulfonic acid, benzenesulfonic acid, p-toluenesulfonic acid, 2,4,6-trimethylbenzenesulfonic acid, 4-n-octylbenzenesulfonic acid, 5-methyl-2-naphthalenesulfonic acid, 8-t-butyl-1,5-naphthalenedisulfonic acid, 5-phenyl-1,3-benzenedisulfonic acid and 4,4'-biphenyldisulfonic acid.

H in formula (2) represents an active hydrogen. Some of the alcohols, thiols, phenols, thiophenols, carboxylic acids and sulfonic acids have a plurality of active hydrogens. Thus, a compound represented by formula (2), all or some of whose active hydrogens act as H in formula (2), falls within those which may be used in the process of this invention.

In this invention, in the presence of a phosphine oxide represented by formula (1), an epoxy compound is also reacted with a carboxylate represented by formula (3), a carboxylic anhydride represented by formula (4) or a sulfonate represented by formula (5):

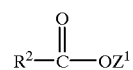

Formula (3)

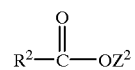

Formula (4)

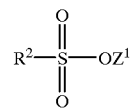

Formula (5)

where in formulas (3), (4) and (5) $R^2$ is hydrogen or an organic group having 1 to 35 carbon atoms; in formulas (3) and (5) $OZ^1$ is an organic moiety of the alcohol or phenol except the active hydrogen; and in formula (4) $OZ^2$ is an organic moiety of the carboxylic acid except the active hydrogen, to form an oxyalkylene derivative having a substructure represented by formula (8), (9) or (10), respectively:

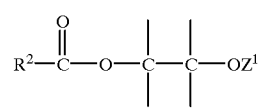

Formula (8)

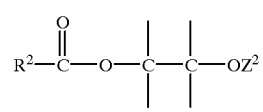

Formula (9)

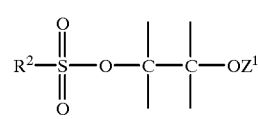

Formula (10)

Briefly, an epoxy compound is reacted with a carboxylate represented by formula (3), a carboxylic anhydride represented by formula (4) or a sulfonate represented by formula (5), to prepare an oxyalkylene derivative having a substructure represented by formula (8), (9) or (10), respectively.

$R^2$ in the carboxylate represented by formula (3), the carboxylic anhydride represented by formula (4) and the sulfonate represented by formula (5) is hydrogen or an organic group having 1 to 35 carbon atoms. An organic group having 1 to 35 carbon atoms herein means a hydrocarbon group having 1 to 35 carbon atoms; an organic group having 2 to 35 carbon atoms and at least one carboxylate group; an organic group having 2 to 35 carbon atoms and at least one carboxylic anhydride group; or an organic group having 3 to 35 carbon atoms and at least one sulfonate group.

Specifically, $R^2$ includes hydrogen and a hydrocarbon group having 1 to 35 carbon atoms; for example, alkyl groups having 1 to 35 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl and pentatriacontyl; cycloalkyl groups having 3 to 35 carbon atoms such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, 2,3,4,5,6,7-hexahydroindenyl, 2-norbonyl, 5-norbornen-2-yl and adamantyl; alkenyl groups having 2 to 35 carbon atoms such as vinyl, isopropenyl, allyl, 1-butenyl, 2-butenyl, 3-butenyl, 1-pentenyl, 2-pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl; alkynyl groups having 2 to 35 carbon atoms such as ethynyl, propynyl, butynyl, pentynyl, hexynyl, heptynyl, octynyl, nonynyl, decynyl, undecynyl, dedecynyl, tridecynyl, tetradecynyl, pentadecynyl, hexadecynyl, heptadecynyl, octadecynyl, nonadecynyl and eicosynyl; and aryl groups having 6 to 35 carbon atoms such as phenyl, tolyl, 2-ethylphenyl, 4-tert-butylphenyl, 4-nonylphenyl, 2-cyclohexylphenyl, 4-vinylphenyl, 4-isopropenylphenyl, 3-phenylphenyl, 1-naphthyl, 2-naphthyl, 5-methyl-1-naphthyl, 6-vinyl-2-naphthyl, anthracen-1-yl, phenanthren-1-yl, 1-(1-naphthyl)-2-naphthyl, 4-chlorophenyl, pentafluorophenyl, 2,6-dibromophenyl, 2,4-diiodophenyl, 5-fluoro-1-naphthyl and 6-bromo-2-naphthyl.

$R^2$ also includes an organic group having 2 to 35 carbon atoms and at least one carboxylate group; for example, aliphatic hydrocarbon groups having 3 to 35 carbon atoms and at least one carboxylate group such as methoxycarbonylmethyl, 2-(4-chlorophenoxycarbonyl) ethyl, 10-(methoxycarbonyl)decyl, 4-(n-octyloxycarbonyl) butyl, 2-(4-phenoxyphenoxycarbonyl)-1-methylethyl, 8-(cyclohexyloxycarbonyl)octyl, 10-(phenoxycarbonyl) decyl, 10-(n-octyloxycarbonyl)decyl, 2,3-bis(1-naphthoxycarbonyl)-1-methylpropyl, 2,3,4-tris(n-nonyloxycarbonyl)butyl, 2-(methoxycarbonyl)cyclopropyl, 4-(isopropoxycarbonyl)cyclohexyl, 3-(phenoxycarbonyl) cyclopentyl, 3,5-bis(ethoxycarbonyl)cyclohexyl, 4-(4-methoxycarbonylphenyl)cyclohexyl, 3-cyclohexyloxycarbonyl-bicyclo[2.2.1]heptan-2-yl, 5-(4-fluorophenoxycarbonyl)bicyclo[2.2.1]heptan-2-yl, 5-(4-fluorophenoxycarbonyl)bicyclo[2.2.1]heptan-3-yl, 3,4-bis(4-methoxybutyloxycarbonyl)cyclohexyl, 3,5-bis(n-octyloxycarbonyl)cyclohexyl, 4-(n-eicosyloxycarbonyl) cyclohexyl and 2,3,4-tris(n-nonyloxycarbonyl)cyclopentyl; aromatic hydrocarbon groups having 8 to 35 carbon atoms and at least one carboxylate group such as 4-methoxycarbonylphenyl, 3-ethoxycarbonyl-5-methylphenyl, 4-(4-methoxycarbonylphenyl)phenyl, 4-(2-phenoxycarbonylvinyl)phenyl, 6-n-butoxycarbonyl-2-yl, 3,4,5-tris(ethoxycarbonyl)phenyl, 3,4-bis(n-butoxycarbonyl)phenyl, 3,5-bis(n-octyloxycarbonyl)phenyl, 4-[3,5-bis(n-decyloxycarbonyl)phenyl]phenyl and 3,4-bis(4-phenylphenyl)phenyl; and substituted carboxy groups having 2 to 35 carbon atoms such as methoxycarbonyl, 4-ethoxybutoxycarbonyl, cyclohexyloxycarbonyl, phenoxycarbonyl, n-decyloxycarbonyl, 1-naphthoxycarbonyl, 8-benzoyloxyoctyloxycarbonyl and 1-decanoyloxymethyl-2-decanoyloxyethyloxycarbonyl.

$R^2$ also includes an organic group having 2 to 35 carbon atoms and at least one carboxylic anhydride group; for example, aliphatic hydrocarbon groups having 3 to 35 carbon atoms and at least one carboxylic anhydride group such as formyloxycarbonylmethyl, 2-acetoxycarbonylvinyl, tetrahydrofuran-2,5-dion-3-ylmethyl, anhydrous cyclohexane-3,4-dicarboxyl-1-yl, anhydrous bicyclo[2.2.1]heptane-2,3-dicarboxyl-5-yl, anhydrous bicyclo[2.2.1] heptan-7-oxa-2,3-dicarboxyl-5-yl, 4-(n-octanoyloxycarbonyl)butyl, 10-(benzoyloxycarbonyl)decyl, 3,4-bis(cyclohexyloxycarbonyl)-2-ethylbutyl, 3,4-bis(decanoyloxycarbonyl)cyclohexyl, 2,3,4-tris(n-octanoyloxycarbonyl)butyl and 2,3,5-tris(n-octanoyloxycarbonyl)cyclopentyl; aromatic hydrocarbon groups having 8 to 35 carbon atoms and at least one carboxylic anhydride group such as 4-formyloxycarbonylphenyl, anhydrous fumar-5-yl, 4-(2-n-butyroyloxycarbonylvinyl)phenyl, anhydrous naphthalene-5,6-dicarboxyl-1-yl, 4-octanoyloxycarbonylphenyl and 6-(n-eicosanoyloxycarbonyl)-1-chloro-2-yl; and substituted carbonyloxycarbonyl groups having 2 to 35 carbon atoms such as formyloxycarbonyl, cyclohexylcarbonyloxycarbonyl, benzoyloxycarbonyl and 1-naphthoyloxycarbonyl.

$R^2$ also includes an organic group having 3 to 35 carbon atoms and at least one sulfonate group: for example, such as 2-methoxysulfonylethyl, 4-(n-butoxysulfonyl)butyl, 4-(n-octyloxysulfonyl)cyclohexyl, 4-phenoxysulfonylphenyl and 6-(n-octyloxysulfonyl)cyclohexyl.

The organic groups having 1 to 35 carbon atoms may have any other substituent and/or hetero atom as long as it does not adversely affect the process of this invention.

Preferably $R^2$ may be selected from alkyl groups having 1 to 35 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl and pentatriacontyl; alkenyl groups having 2 to 35 carbon atoms such as vinyl, isopropenyl, allyl, 1-butenyl, 2-butenyl, 3-butenyl, 1-pentenyl, 2-pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl; aryl groups having 6 to 35 carbon atoms such as phenyl, tolyl, 2-ethylphenyl, 4-tert-butylphenyl, 4-nonylphenyl, 2-cyclohexylphenyl, 4-vinylphenyl, 4-isopropenylphenyl, 3-phenylphenyl, 1-naphthyl, 2-naphthyl, 5-methyl-1-naphthyl, 6-vinyl-2-naphthyl, anthracen-1-yl, phenanthren-1-yl, 1-(1-naphthyl)-2-naphthyl, 4-chlorophenyl, pentafluorophenyl, 2,6-dibromophenyl, 2,4-diiodophenyl, 5-fluoro-1-naphthyl and 6-bromo-2-naphthyl; aliphatic hydrocarbon groups having 3 to 35 carbon atoms and at least one carboxylate group such as methoxycarbonylmethyl, 2-(4-chlorophenoxycarbonyl) ethyl, 10-(methoxycarbonyl)decyl, 4-(n-octyloxycarbonyl) butyl, 2-(4-phenoxyphenoxycarbonyl)-1-methylethyl, 8-(cyclohexyloxycarbonyl)octyl, 10-(phenoxycarbonyl) decyl, 10-(n-octyloxycarbonyl)decyl, 2,3-bis(1-naphthoxycarbonyl)-1-methylpropyl, 2,3,4-tris(n-nonyloxycarbonyl)butyl, 2-(methoxycarbonyl)cyclopropyl, 4-(isopropoxycarbonyl)cyclohexyl, 3-(phenoxycarbonyl) cyclopentyl, 3,5-bis(ethoxycarbonyl)cyclohexyl, 4-(4-methoxycarbonylphenyl)cyclohexyl, 3-cyclohexyloxycarbonyl-bicyclo[2.2.1]heptan-2-yl, 5-(4-fluorophenoxycarbonyl)bicyclo[2.2.1]heptan-2-yl, 5-(4-fluorophenoxycarbonyl)bicyclo[2.2.1]heptan-3-yl, 3,4-bis(4-methoxybutyloxycarbonyl)cyclohexyl, 3,5-bis(n-octyloxycarbonyl)cyclohexyl, 4-(n-eicosyloxycarbonyl) cyclohexyl and 2,3,4-tris(n-nonyloxycarbonyl)cyclopentyl; aromatic hydrocarbon groups having 8 to 35 carbon atoms and at least one carboxylate group such as 4-methoxycarbonylphenyl, 3-ethoxycarbonyl-5-methylphenyl, 4-(4-methoxycarbonylphenyl)phenyl, 4-(2-phenoxycarbonylvinyl)phenyl, 6-n-butoxycarbonyl-2-yl, 3,4,5-tris(ethoxycarbonyl)phenyl, 3,4-bis(n- butoxycarbonyl)phenyl, 3,5-bis(n-octyloxycarbonyl)phenyl, 4-[3,5-bis(n-decyloxycarbonyl)phenyl]phenyl and 3,4-bis (4-phenylphenyl)phenyl; and aromatic hydrocarbon groups having 8 to 35 carbon atoms and at least one carboxylic anhydride group such as 4-formyloxycarbonylphenyl, anhydrous fumar-5-yl, 4-(2-n-butyroyloxycarbonylvinyl)phenyl, anhydrous naphthalene-5,6-dicarboxyl-1-yl, 4-octanoyloxycarbonylphenyl and 6-(n-eicosanoyloxycarbonyl)-1-chloro-2-yl.

More preferably $R^2$ may be selected from alkyl groups having 1 to 6 carbon atoms such as methyl, ethyl, propyl, butyl, pentyl and hexyl; alkenyl groups having 2 to 4 carbon atoms such as vinyl, isopropenyl, allyl, 1-butenyl, 2-butenyl and 3-butenyl; aryl groups having 6 to 10 carbon atoms such as phenyl, tolyl, 2-ethylphenyl, 4-tert-butylphenyl, 4-vinylphenyl, 4-isopropenylphenyl, 1-naphthyl, 2-naphthyl, 4-chlorophenyl, pentafluorophenyl, 2,6-dibromophenyl, 2,4-diiodophenyl, 5-fluoro-1-naphthyl and 6-bromo-2-naphthyl; aliphatic hydrocarbon groups having 3 to 13 carbon atoms and at least one carboxylate group such as methoxycarbonylmethyl, 2-(4-chlorophenoxycarbonyl) ethyl, 10-(methoxycarbonyl)decyl, 4-(n-octyloxycarbonyl) butyl, 2-(methoxycarbonyl)cyclopropyl, 4-(isopropoxycarbonyl)cyclohexyl, 3-(phenoxycarbonyl) cyclopentyl and 3,5-bis(ethoxycarbonyl)cyclohexyl; aromatic hydrocarbon groups having 8 to 16 carbon atoms and at least one carboxylate group such as 4-methoxycarbonylphenyl, 3-ethoxycarbonyl-5-methylphenyl, 4-(4-methoxycarbonylphenyl)phenyl, 4-(2-phenoxycarbonylvinyl)phenyl, 6-n-butoxycarbonyl-2-yl, 3,4,5-tris(ethoxycarbonyl)phenyl and 3,4-bis(n-butoxycarbonyl)phenyl; and aromatic hydrocarbon groups having 8 to 16 carbon atoms and at least one carboxylic anhydride group such as 4-formyloxycarbonylphenyl, anhydrous fumar-5-yl, 4-(2-n-butyroyloxycarbonylvinyl)phenyl, anhydrous naphthalene-5,6-dicarboxyl-1-yl and 4-octanoyloxycarbonylphenyl.

$OZ^1$ in the carboxylate represented by formula (3) and the sulfonate represented by formula (5) in this invention is an organic moiety of an alcohol or phenol except its active hydrogen.

Alcohols giving the organic group $OZ^1$ include aliphatic and alicyclic alcohols consisting of carbon and hydrogen atoms and an oxygen atom in the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, docosanol, hexacosanol, triacontanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, β-citronellol, dihydromyrcenol, oleyl alcohol, nerolidol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol, glycerol, poly(vinyl alcohol), cyclobutanol, cyclopentanol, cyclohexanol, 2-methylcyclohexanol, menthol, cycloheptanol, cyclooctanol, cyclododecanol, norborneol, borneol, decahydro-1-naphthol, 1-adamantanol, 2-cyclohexen-1-ol, terpinen-4-ol, carveol, 5-norbonen-2-ol and ergocalciferol; halogenated aliphatic and alicyclic alcohols such as 2-fluoroethanol, 2-chloropropanol, 3-chloro-2, 2-dimethylpropanol, 6-chloro-1-hexanol, 2,2,3,3-tetrafluoropropanol, 2-chloro-2-propen-1-ol, 4-chlorobenzyl alcohol, 3-(6-chloro-1-naphthyl)propanol and 2-chlorocyclohexanol; aliphatic and alicyclic alcohols having an ether bond such as 2-methoxyethanol, 1-methoxy-2-propanol, 3-cyclohexyloxy-1-propanol, diethylene glycol monomethyl ether, dipropylene glycol monomethyl ether, diethylene glycol, dipropylene glycol, triethylene glycol, poly(oxypropylene) triol, 2-ethoxybenzyl alcohol, 3-phenoxybenzyl alcohol, 6-methoxy-2-naphthalenethanol, tetrahydro-4H-pyran-4-ol and 1,4-dioxan-2,3-diol; aliphatic and alicyclic alcohols having an ester bond such as 3-acetoxy-1-propanol, 2-(3-methylbenzoyloxy)-1-ethanol, 4-hydroxybutyl methacrylate, 3-acetoxycinnamic alcohol, 2-hydroxyethyl 3-(2-hydroxyethyloxy)benzoate, bis(2-hydroxypropyl) succinate, 3-methoxycarbonylcyclohexanol, 4-vinyloxycarbonylcyclohexanol, poly(lactic acid), poly(ε-caprolactone) and bis(2-hydroxyethyl)terephthalate; aliphatic and alicyclic alcohols having an amide bond such as N-(2-hydroxyethyl)acetamide, 3-(dimethylcarbamoyl)-1-propanol, N-(3-hydroxypropyl)acrylamide, N-(4-hydroxycyclohexyl)benzamide and di-N-(2-hydroxyethyl) phthalamide. These compounds may have any other substituent as long as it does not adversely affect the process of this invention.

Preferably they may be aliphatic alcohols consisting of carbon and hydrogen atoms and an oxygen atom of the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, docosanol, hexacosanol, triacontanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, β-citronellol, dihydromyrcenol, oleyl alcohol, nerolidol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol, glycerol and poly(vinyl alcohol); and aliphatic alcohols having an ether bond such as 2-methoxyethanol, 1-methoxy-2-propanol, 3-cyclohexyloxy-1-propanol, diethylene glycol monomethyl ether, dipropylene glycol monomethyl ether, diethylene glycol, dipropylene glycol, triethylene glycol, poly(oxypropylene)triol, 2-ethoxybenzyl alcohol, 3-phenoxybenzyl alcohol and 6-methoxy-2-naphthalenethanol.

More preferably they may be aliphatic alcohols having 1 to 20 carbon atoms consisting of carbon and hydrogen atoms and an oxygen atom of the alcoholic hydroxyl group such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, allyl alcohol, 2-methyl-2-propen-1-ol, crotyl alcohol, 3-buten-1-ol, 3-methyl-2-buten-1-ol, 2-penten-1-ol, 4-methyl-3-penten-1-ol, 2-hexen-1-ol, 6-methyl-5-hepten-2-ol, 1-octen-3-ol, 1,6-pentadien-4-ol, 2,4-dimethyl-2,6-heptadien-1-ol, nerol, geraniol, linalool, 8,10-dodecadien-1-ol, farnesol, benzyl alcohol, phenethyl alcohol, diphenylpropanol, phenylbutanol, ethylene glycol, propylene glycol and glycerol.

Phenols giving the organic group $OZ^1$ include phenols consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6- diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tris(4-hydroxyphenyl)methane, phenol novolak, poly(4-hydroxystyrene) and poly(4-hydroxy-α-methylstyrene); halogenated phenols such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol; phenols having an ether bond such as 2-ethoxyphenol, 4-(phenoxymethyl)phenol, 3,4,5-trimethoxyphenol, 7-methoxy-2-naphthol, 4-benzyloxy-3-methoxyphenol and 3,3'-(ethylenedioxy)diphenol; phenols having a keto group such as 3-hydroxyacetophenone, 2-(2-oxopropyl)phenol, 4-hydroxybenzophenone, 1-hydroxy-2-acenaphthone, 4,4'-dihydroxybenzophenone, 2,6-dihydroxyacetophenone and phloretin; phenols having an ester bond such as 4-acetoxymethylphenol, methyl salicylate, 4-hydroxybenzyl acrylate, ethyl 4-hydroxy-3-methoxycinnamate, 2-methoxycarbonyl-6-methyl-3-naphthol, 1,2-bis(4-hydroxybenzoyloxy)ethane and ethyl 3,4,5-trihydroxybenzoate; and phenols having an amide bond such as 4-acetaminophenol, 3-(N,N-dimethylcarbamoyl)phenol, 4-(N,N-dimethylcarbamoyl)-3-methylphenol, N-(3-hydroxy-5-methyl)phenylacrylamide, N-(5-hydroxy-8-methyl-2-naphthyl)methacrylamide, N-(4-hydroxybenzyl)benzamide and N,N'-bis(4-hydroxyphenyl)-5-methyl-1,3-benzenedicarboxamide. These compounds may have any other substituent as long as it does not adversely affect the process of this invention.

Preferably they include phenols consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tris(4-hydroxyphenyl)methane, phenol novolak, poly(4-hydroxystyrene) and poly(4-hydroxy-α-methylstyrene); and halogenated phenols such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol.

More preferably it may be selected from phenols having 6 to 27 carbon atoms consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene and tris(4-hydroxyphenyl)methane.

$OZ^2$ in the carboxylic anhydride represented by formula (4) in this invention is an organic moiety of a carboxylic acid except its active hydrogen.

Carboxylic acids giving the organic group $OZ^2$ include aliphatic, alicyclic and aromatic carboxylic acids consisting of carbon and hydrogen atoms and an oxygen atom of the carboxyl group such as formic acid, acetic acid, propionic acid, butyric acid, isobutyric acid, acrylic acid, methacrylic acid, lauric acid, stearic acid, oleic acid, phenylacetic acid, cyclohexane carboxylic acid, benzoic acid, p-methylbenzoic acid, 2-naphthalene carboxylic acid, 2-norbornane carboxylic acid, 2-norbornene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid, poly (methacrylic acid) and pyromellitic acid; halogenated aliphatic, alicyclic and aromatic carboxylic acids such as 4-chlorobutyric acid, 5-fluoro-2-hexanoic acid, pentafluorophenylacetic acid, 4-chlorobenzoic acid, 3-bromocyclohexane carboxylic acid, 5-chloro-2-bicyclo[2.2.1]hexane carboxylic acid and 6-iodo-1-naphthalene carboxylic acid; aliphatic, alicyclic and aromatic carboxylic acids having an ether bond such as methoxyacetic acid, 4-(4-methylphenoxy)butyric acid, 3-phenoxyphenylacetic acid, 2,2'-ethylenedioxy-diacetic acid, 3-benzyloxycyclohexane carboxylic acid, 5,6-dimethoxy-2-bicyclo[2.2.1]hexane carboxylic acid, 3-phenoxycinnamic acid, 5-methoxyisophthalic acid and 4,4'-ethylenedioxybenzoic acid; aliphatic, alicyclic and aromatic carboxylic acids having an ester bond such as 4-acetoxybutyric acid, monoisopropyl succinate, monomethyl fumarate, monoethyl 1,3-cyclohexane dicarboxylate, monohexyl 2,6-norbornane dicarboxylate, 4-hydroxycarbonylbenzyl acrylate, cyclohexyl 5-methyl-1,3-benzene dicarboxylate, poly(lactic acid), poly(ε-caprolactone) and 1,2-bis(4-hydroxycarbonylbenzoyloxy)ethane; and aliphatic, alicyclic and aromatic carboxylic acids having an amide bond such as N-acetylalanine, 3-(N,N-dimethylcarbamoyl)propionic acid, N-methacryloylphenylglycine, N-(4-hydroxycyclohexyl)benzamide, 5-(N,N-diethylcarbamoyl)-1-naphthalene carboxylic acid and N,N'-(4-hydroxyphenyl)terephthalamide. These compounds may have any other substituent as long as it does not adversely affect the process of this invention.

Preferably they include aliphatic and aromatic carboxylic acids consisting of carbon and hydrogen atoms and an oxygen atom of the carboxyl group such as formic acid, acetic acid, propionic acid, butyric acid, isobutyric acid, acrylic acid, methacrylic acid, lauric acid, stearic acid, oleic acid, phenylacetic acid, benzoic acid, p-methylbenzoic acid, 2-naphthalene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid, poly(methacrylic acid) and pyromellitic acid.

More preferably they include aliphatic carboxylic acids having 1 to 12 carbon atoms and aromatic carboxylic acid having 7 to 12 carbon atoms consisting of carbon and hydrogen atoms and an oxygen atom of the carboxyl group such as formic acid, acetic acid, propionic acid, butyric acid, isobutyric acid, acrylic acid, methacrylic acid, lauric acid, phenylacetic acid, benzoic acid, p-methylbenzoic acid, 2-naphthalene carboxylic acid, oxalic acid, malonic acid, succinic acid, maleic acid, fumaric acid, adipic acid, itaconic acid, butane tetracarboxylic acid, phthalic acid, isophthalic acid, terephthalic acid, trimellitic acid and pyromellitic acid.

More preferable carboxylates represented by formula (3) are those where $R^2$ is alkyl group having 1 to 6 carbon atoms, alkenyl group having 2 to 4 carbon atoms, aryl group having 6 to 10 carbon atoms, aliphatic hydrocarbon group having 3 to 13 carbon atoms and at least one carboxylate group, or aromatic hydrocarbon group having 8 to 16 carbon atoms and at least carboxylate group; and $OZ^1$ is an organic group derived from an aliphatic alcohol having 1 to 20 carbon atoms consisting of carbon and hydrogen atoms and an oxygen atom of an alcoholic hydroxyl group or a phenol having 6 to 27 carbon atoms consisting of carbon and hydrogen atoms and an oxygen atom of a phenolic hydroxyl group.

More preferable carboxylic anhydride represented by formula (4) are those where $R^2$ is alkyl group having 1 to 6 carbon atoms, aryl group having 6 to 10 carbon atoms or aromatic hydrocarbon group having 8 to 16 carbon atoms and at least carboxylic anhydride group; and $OZ^2$ is an organic group derived from an aliphatic carboxylic acid having 1 to 12 carbon atoms or aromatic carboxylic acid having 7 to 12 carbon atoms consisting of carbon and hydrogen atoms and an oxygen atom of a carboxyl group.

More preferable sulfonates represented by formula (5) are those where $R^2$ is alkyl having 1 to 6 carbon atoms or aryl having 6 to 10 carbon atoms; and $OZ^1$ is an organic group derived from an aliphatic alcohol having 1 to 20 carbon atoms consisting of carbon and hydrogen atoms and an oxygen atom of an alcoholic hydroxyl group or a phenol having 6 to 27 carbon atoms consisting of carbon and hydrogen atoms and an oxygen atom of a phenolic hydroxyl group.

The carboxylate represented by formula (3) and the sulfonate represented by formula (5) have been illustrated as an alcohol or phenol giving $OZ^1$ whose one active hydrogen has been substituted with $R^2C(O)-$ and $R^2SO_2-$, respectively. However, alcohols or phenols having a plurality of active hydrogens may be used. A compound, all or some of whose active hydrogens are substituted with $R^2C(O)-$ or $R^2SO_2-$, falls within the carboxylate represented by formula (3) or the sulfonate represented by formula (5) in the process of this invention.

The carboxylic anhydride represented by formula (4) has been illustrated as a carboxylic acid giving $OZ^2$ whose one active hydrogen in its carboxyl group has been substituted with $R^2C(O)-$. However, carboxylic acids having a plurality of active hydrogens may be used. A compound, all or some of whose active hydrogens are substituted with $R^2C$ (O)—, falls within the carboxylic anhydride represented by formula (4) in the process of this invention.

In this invention, in the presence of a phosphine oxide represented by formula (1), an epoxy compound is also reacted with a carbonate represented by formula (6)

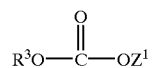

Formula (6)

where $R^3$ is aliphatic hydrocarbon group having 1 to 35 carbon atoms or aromatic hydrocarbon group having 6 to 35 carbon atoms, and $OZ^1$ is as defined above for formula (3) and (5), to form an oxyalkylene derivative having a substructure represented by formula (11) and/or a substructure represented by formula (12):

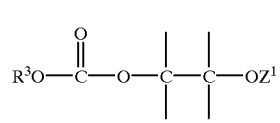

Formula (11)

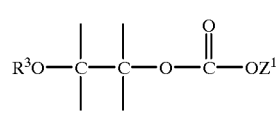

Formula (12)

In this process, the reaction of the epoxy compound with the carbonate represented by formula (6) gives one or both of the oxyalkylene derivatives having the substructures represented by formulas (11) and (12). The yield ratio between these oxyalkylene derivatives may depend on a specific combination of $R^3$ and $OZ^1$ in the carbonate represented by formula (6).

When $R^3$ in the carbonate represented by formula (6) is aliphatic hydrocarbon group having 1 to 35 carbon atoms, $OZ^1$ as an organic group derived from an alcohol gives both oxyalkylene derivatives having the substructures represented by formulas (11) and (12) in similar yield, while $OZ^1$ as an organic group derived from a phenol gives an oxyalkylene derivative having the substructure represented by formula (11) as a main product. When $R^3$ in the carbonate represented by formula (6) is aromatic hydrocarbon group having 6 to 35 carbon atoms, $OZ^1$ as an organic group derived from an alcohol gives an oxyalkylene derivative having the substructure represented by formula (12) as a main product, while $OZ^1$ as an organic group derived from a phenol gives both oxyalkylene derivatives having the substructures represented by formulas (11) and (12) in similar yields.

For $R^3$ in the carbonate represented by formula (6), an aliphatic hydrocarbon group having 1 to 35 carbon atoms may be selected from alkyls having 1 to 35 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl and pentatriacontyl; cycloalkyls having 3 to 35 carbon atoms such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, 2,3,4,5,6,7-hexahydroindenyl, 2-norbonyl, 5-norbornen-2-yl and adamantyl; and alkenyl groups having 2 to 35 carbon atoms such as vinyl, isopropenyl, allyl, 1-butenyl, 2-butenyl, 3-butenyl, 1-pentenyl, 2-pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl.

Preferably it may be selected from alkyl groups having 1 to 35 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl and pentatriacontyl.

More preferably it may be selected from alkyls having 1 to 6 carbon atoms such as methyl, ethyl, propyl, butyl, pentyl, hexyl.

For $R^3$ in the carbonate represented by formula (6), an aromatic hydrocarbon group having 6 to 35 carbon atoms may be selected from phenyl, tolyl, 2-ethylphenyl, 4-tert-butylphenyl, 4-nonylphenyl, 2-cyclohexylphenyl, 4-vinylphenyl, 4-isopropenylphenyl, 3-phenylphenyl, 1-naphthyl, 2-naphthyl, 5-methyl-1-naphthyl, 6-vinyl-2-naphthyl, anthracen-1-yl, phenanthren-1-yl, 1-(1-naphthyl)-2-naphthyl, 4-chlorophenyl, pentafluorophenyl, 2,6-dibromophenyl, 2,4-diiodophenyl, 5-fluoro-1-naphthyl and 6-bromo-2-naphthyl. These compounds may have any other substituent as long as it does not adversely affect the process of this invention.

Preferably it may be selected from aromatic hydrocarbon groups having 6 to 12 carbon atoms such as phenyl, tolyl, 2-ethylphenyl, 4-tert-butylphenyl, 2-cyclohexylphenyl, 4-vinylphenyl, 4-isopropenylphenyl, 3-phenylphenyl, 1-naphthyl, 2-naphthyl, 5-methyl-1-naphthyl, 6-vinyl-2-naphthyl, 4-chlorophenyl, pentafluorophenyl, 2,6-dibromophenyl, 2,4-diiodophenyl, 5-fluoro-1-naphthyl and 6-bromo-2-naphthyl.

More preferably it may be selected from aromatic hydrocarbon groups having 6 to 9 carbon atoms such as phenyl, tolyl, 2-ethylphenyl, 4-vinylphenyl, 4-isopropenylphenyl, 4-chlorophenyl, pentafluorophenyl, 2,6-dibromophenyl and 2,4-diiodophenyl.

$OZ^1$ in the carbonate represented by formula (6) is as defined for formulas (3) and (5).

More preferable carbonates represented by formula (6) are those where $R^3$ is alkyl having 1 to 6 carbon atoms or aromatic hydrocarbon groups having 6 to 9 carbon atoms; and $OZ^1$ is an organic group derived from an aliphatic alcohol having 1 to 20 carbon atoms consisting of carbon and hydrogen atoms and an oxygen atom of an alcoholic hydroxyl group or a phenol having 6 to 27 carbon atoms consisting of carbon and hydrogen atoms and an oxygen atom of a phenolic hydroxyl group.

The carbonate represented by formula (6) has been illustrated as an alcohol or phenol giving $OZ^1$ whose one active hydrogen has been substituted with $R^3OC(O)$—. Alcohols or phenols having a plurality of active hydrogens may be used. A compound, all or some of whose active hydrogens are substituted with $R^3OC(O)$, falls within the carbonate represented by formula (6) in the process of this invention.

In the process of this invention, of the compounds listed as an epoxy compound, those having an ester bond may be classified either into an epoxy compound or into a carboxylate, i.e., these may be used as either type of starting material. When the epoxy compound having an ester bond is reacted with a compound represented by formula (2), (3), (4), (5) or (6), whether the epoxy group in the epoxy compound reacts with the ester moiety in the epoxy compound or with the compound represented by formula (2), (3), (4), (5) or (6), may vary depending on difference in reactivity of the compounds used. Furthermore, when two or more of the compounds represented by formulas (2) to (6) are used in combination or when a compound which may be classified into two or more of formulas (2) to (6) are used, a substructure which an oxyalkylene derivative as a product has may depend on difference in reactivity of individual compounds used.

In the process of this invention, an epoxy compound is reacted with i) an alcohol, thiol, phenol, thiophenol, carboxylic acid or sulfonic acid represented by formula (1);

ii) a carboxylate represented by formula (3), a carboxylic anhydride represented by formula (4) or a sulfonate represented by formula (5); or iii) a carbonate represented by formula (6) in the presence of a phosphine oxide represented by formula (1).

This reaction may be conducted, for example, by adding, in one portion, intermittently or continuously, an epoxy compound to a mixture of a phosphine oxide represented by formula (1) and a compound represented by formula (2), (3), (4), (5) or (6) in, if used, a solvent, or by adding a phosphine oxide represented by formula (1) in a mixture of an epoxy compound and a compound represented by formula (2), (3), (4), (5) or (6) in, if used, a solvent.

The amount of the alcohol, thiol, phenol, thiophenol, carboxylic acid or sulfonic acid represented by formula (2) is generally selected so as to make the amount of the active hydrogen(s) in the compound 0.5 to 1.5 mol, preferably 0.7 to 1.3 mol per 1 mol of the epoxy group in the epoxy compound.

The amount of the carboxylate represented by formula (3), the carboxylic anhydride represented by formula (4) or the sulfonate represented by formula (5) is generally selected so as to make the amount of $R^2C(O)$— or $R^2SO_2$— in the compound 0.5 to 1.5 mol, preferably 0.7 to 1.3 mol per 1 mol of the epoxy group in the epoxy compound.

The amount of the carbonate represented by formula (6) is generally selected so as to make the amount of $R^3OC(O)$— in the carbonate represented by formula (6) 0.5 to 1.5 mol, preferably 0.7 to 1.3 mol per 1 mol of the epoxy group in the epoxy compound.

In any case, the amount of the phosphine oxide may be, but not limited to, generally below 0.5 mol, preferably $1\times10^{-5}$ to 0.1 mol, more preferably $1\times10^{-4}$ to 0.05 mol per 1 mol of the epoxy group in the epoxy compound.

A reaction temperature may vary depending on types of materials used and of the phosphine oxide represented by formula (1), but generally below 200° C., preferably 10 to 180° C., more preferably 30 to 150° C. A reaction pressure may be, in any case, vary depending on types of materials used, but generally below 3.0 MPa (absolute pressure; same in the following description). A reaction duration may be generally up to 48 hours, preferably 0.01 to 24 hours, more preferably 0.02 to 10 hours. The reaction system may be, if necessary, replaced with an inert gas such as nitrogen and argon.

In the process of this invention, a solvent may be, if necessary, used. Solvents which may be used include aliphatic or alicyclic hydrocarbon such as n-pentane, n-hexane and cyclohexane; ethers such as dimethyl ether, diethyl ether, diisopropyl ether, dibutyl ether, tetrahydrofuran, 1,4-dioxane, ethylene glycol dimethyl ether, diethylene glycol dimethyl ether, anisole, o-dimethoxybenzene, ethyl phenyl ether, butyl phenyl ether and o-diethoxybenzene; aromatic hydrocarbons such as benzene, toluene, xylenes, ethylbenzene, cumene, mesitylene, tetralin, butylbenzene, p-cymene, diethylbenzene, diisopropylbenzene, triethylbenzene, cyclohexylbenzene, dipentylbenzene and dodecylbenzene; halogenated aromatic hydrocarbons such as chlorobenzene, o-dichlorobenzene, m-dichlorobenzene, 1,2,4-trichlorobenzene, bromobenzene, o-dibromobenzene, bromochlorobenzene, o-chlorotoluene, p-chlorotoluene, p-chloroethylbenzene and 1-chloronaphthalene; and aprotic polar solvents such as dimethyl sulfoxide, N,N-dimethylformamide, hexamethylphosphoramide and N,N'-dimethylimidazolidinone. Any other solvent may be used as long as it does not adversely affect the process of this invention. These solvents may be used alone or in combination.

In any case, an isolation procedure of a desired oxyalkylene derivative from a reaction mixture may vary depending on types of starting materials used, the type of the desired oxyalkylene derivative and the type or amount of a solvent used, but it may be generally isolated by distillation, recrystallization or column chromatography for the reaction mixture or, when a solvent is used, a residue after evaporating the solvent.

As described above, in the presence of a phosphine oxide represented by formula (1), an epoxy compound may be reacted with i) an alcohol, thiol, phenol, thiophenol, carboxylic acid or sulfonic acid represented by formula (2):

H—Q    Formula (2)

to give an oxyalkylene derivative having a substructure represented by formula (7):

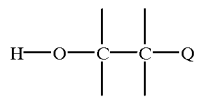

Formula (7)

ii) a carboxylate represented by formula (3), a carboxylic anhydride represented by formula (4) or a sulfonate represented by formula (5):

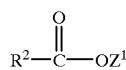

Formula (3)

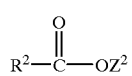

Formula (4)

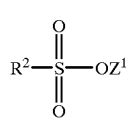

Formula (5)

to give an oxyalkylene derivative having a substructure represented by formula (8), (9) or (10), respectively:

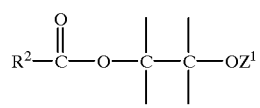

Formula (8)

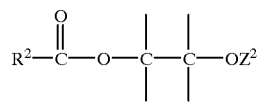

Formula (9)

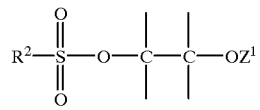

Formula (10)

or iii) a carbonate represented by formula (6):

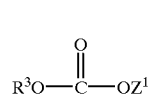

Formula (6)

to give an oxyalkylene derivative having a substructure represented by formulas (11) and/or (12):

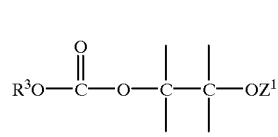

Formula (11)

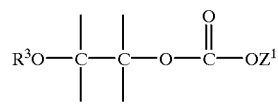

Formula (12)

with a quite high catalyst activity, in a high yield.

This invention will be specifically described with reference to examples. It should be, however, noted that these are not limiting, but only illustrative.

EXAMPLE 1

In a 100 mL pear-shaped flask were precisely weighed 0.579 g of tris[tris(dimethylamino)phosphoranylideneamino]phosphine oxide ([(Me$_2$N)$_3$P=N]$_3$P=O where Me is methyl, same in the following description) as a phosphine oxide represented by formula (1) which was substantially anhydrous by adequate drying over phosphorous pentoxide in a desiccator in vacuo (1.00 mmol) and 9.88 g of phenol (105 mmol). To the mixture warmed to 90° C. was added dropwise 15.0 g of phenyl glycidyl ether (referred to as "PGE"; same in the following description) (100 mmol) over 10 min. After addition, the mixture was stirred at the same temperature for 5 hours, and cooled to room temperature over about 10 min. A small portion of the reaction mixture was quantitatively analyzed by gas chromatography using 1,3,5-trichlorobenzene as an internal standard, indicating that the starting PGE had been almost completely consumed to form desired 1,3-diphenoxy-2-propanol in a yield of 96% based on PGE. In brief, the reaction almost quantitatively proceeded. The reaction mixture was directly subjected to column chromatography to give 22.5 g of 1,3-diphenoxy-2-propanol as a colorless solid in an isolation yield of 92% whose various analyses gave data identical to a reference standard. The catalyst activity (molar amount of a desired product per one mole of catalyst in a unit time; same in the following description) of tris[tris(dimethylamino) phosphoranylidene-amino]phosphine oxide was 20 mol/mol/h, which was surprisingly about 3, 2 or 1.5 times as large as that given by boron trifluoride, N-methylimidazole or triphenylphosphine in Comparative Example 2, 3 or 4, respectively.

EXAMPLE 2

A reaction was conducted as described in Example 1 except that tris[tris(dimethylamino)phosphoranylidene-amino]phosphine oxide was replaced with the same molar amount of partially hydrated tris[tris(dimethylamino) phosphoranylidene-amino]phosphine oxide, $[(Me_2N)_3P=N]_3P=O.0.29H_2O$.

As was the situation in Example 1, the starting PGE was almost completely consumed. The product was formed in an analytical yield of 97% and isolated in a yield of 91%. A catalyst activity was 20 mol/mol/h.

Comparative Example 1

A reaction was conducted as described in Example 1 except that tris[tris(dimethylamino)phosphoranylidene-amino]phosphine oxide was absent. The product was formed in an analytical yield of 4%, which was too low to allow 1,3-diphenoxy-2-propanol to be isolated.

Comparative Example 2

A reaction was conducted as described in Example 1 except that tris[tris(dimethylamino)phosphoranylidene-amino]phosphine oxide was replaced with the same molar amount of boron trifluoride-diethyl ether complex, $BF_3.OEt_2$ where Et is ethyl. The product, 1,3-diphenoxy-2-propanol, was formed in an analytical yield of 31% and isolated in a yield of 22%. The catalyst activity was only 6.2 mol/mol/h.

Comparative Example 3

A reaction was conducted as described in Example 1 except that tris[tris(dimethylamino)phosphoranylidene-amino]phosphine oxide was replaced with the same molar amount of N-methylimidazole (NMI in Tables 1 and 2). The product, 1,3-diphenoxy-2-propanol, was formed in an analytical yield of 51% and isolated in a yield of 45%. The catalyst activity was only 10 mol/mol/h.

Comparative Example 4

A reaction was conducted as described in Example 1 except that tris[tris(dimethylamino)phosphoranylidene-amino]phosphine oxide was replaced with the same molar amount of triphenylphosphine (TPP in Table 1). The product, 1,3-diphenoxy-2-propanol, was formed in an analytical yield of 64% and isolated in a yield of 57%. The catalyst activity was only 13 mol/mol/h. The results are shown in Table 1 together with those for Examples 1 and 2 and Comparative Examples 1 to 3.

EXAMPLE 3

A reaction was conducted as described in Example 1 except that tris[tris(dimethylamino)phosphoranylidene-amino]phosphine oxide was replaced with the same molar amount of partially hydrated tris[tris(dimethylamino) phosphoranylidene-amino]phosphine oxide, $[(Me_2N)_3P=N]_3P=O.0.29H_2O$ and phenol was replaced with the same molar amount of phenyl acetate (a compound represented by formula (3) where $R^2$ is methyl and $OZ^1$ is an organic group derived from phenol; same in the following description). Desired 1,3-diphenoxy-2-propyl acetate was formed in an analytical yield of 98% and isolated in a yield of 93%. The catalyst activity was 20 mol/mol/h, which was surprisingly about 15, 6 or 5 times as large as that given by N-methylimidazole, tetrabutylammonium chloride or potassium tert-butoxide in Comparative Example 5, 6 or 7, respectively.

Comparative Example 5

A reaction was conducted as described in Example 3 except that the partially hydrated tris[tris(dimethylamino) phosphoranylidene-amino]phosphine oxide was absent. The product, 1,3-diphenoxy-2-propyl acetate, was formed in an analytical yield of 2%.

Comparative Example 6

A reaction was conducted as described in Example 3 except that the partially hydrated tris[tris(dimethylamino) phosphoranylidene-amino]phosphine oxide was replaced with 10.0 mmol of N-methylimidazole. The product, 1,3-diphenoxy-2-propyl acetate, was formed in an analytical yield of 66% and isolated in a yield of 61%. The catalyst activity was only 1.3 mol/mol/h.

Comparative Example 7

A reaction was conducted as described in Example 3 except that the partially hydrated tris[tris(dimethylamino) phosphoranylidene-amino]phosphine oxide was replaced with 2.50 mmol of tetrabutylammonium chloride. The product, 1,3-diphenoxy-2-propyl acetate, was formed in an analytical yield of 42% and isolated in a yield of 35%. The catalyst activity was only 3.4 mol/mol/h.

Comparative Example 8

A reaction was conducted as described in Example 3 except that the partially hydrated tris[tris(dimethylamino) phosphoranylidene-amino]phosphine oxide was replaced with 2.50 mmol of potassium tertbutoxide. The product, 1,3-diphenoxy-2-propyl acetate, was formed in an analytical yield of 48% and isolated yield of 37%.

The catalyst activity was only 3.9 mol/mol/h. The results are shown in Table 2 together with those from Example 3 and Comparative Examples 5 to 7.

EXAMPLE 4

A reaction was conducted as described in Example 1 except that tris[tris(dimethylamino)phosphoranylidene-amino]phosphine oxide was replaced with the same molar amount of bis[tris(dimethylamino)phosphoranylidene-amino][tris(n-octylmethylamino)phosphoranylidene-amino] phosphine oxide: $[(Me_2N)_3P=N]_2[(n-Oct(Me)N)_3P=N]P=O$ where n-Oct is n-octyl. As was in Example 1, the starting PGE was almost completely consumed. The product, 1,3-diphenoxy-2-propanol, was formed in an analytical yield of 97% and isolated in a yield of 91%.

EXAMPLE 5

A reaction was conducted as described in Example 1 except that tris[tris(dimethylamino)phosphoranylideneamino]phosphine oxide was replaced with the same molar amount of a partially hydrated tris[tris(dimethylamino) phosphoranylidene-amino]phosphine oxide, [(Me$_2$N)$_3$P=N]$_3$P=O.0.29H$_2$O, phenol was replaced with the same molar amount of decanethiol and PGE was replaced with 2,3-epoxynorbornane. Desired 2-decylthio-3-hydroxynorbornane was formed in an analytical yield of 95% and isolated in a yield of 90%.

EXAMPLE 6

In a 300 mL pear-shaped flask were precisely weighed 12.8 g of benzoic acid (105 mmol) and 0.234 g of a partially hydrated tris[tris(dimethylamino)phosphoranylidene-amino]phosphine oxide ([(Me$_2$N)$_3$P=N]$_3$P=O.0.29H$_2$O, and 25.0 g of diglyme was added to the mixture to form a homogeneous solution. To the mixture warmed to 110° C. was added dropwise 15.0 g of PGE (100 mmol) in 25.0 g of diglyme over 30 min. After addition, the mixture was stirred at the same temperature for 5 hours, and cooled to room temperature over about 10 min. A small portion of the reaction solution was quantitatively analyzed by liquid chromatography using 1,3,5-trichlorobenzene, indicating that desired 2-hydroxy-3-phenoxypropyl p-benzoate was formed in an yield of 97% and the reaction almost quantitatively proceeded. The reaction mixture was directly subjected to column chromatography to give 24.2 g of 2-hydroxy-3-phenoxypropyl p-benzoate, whose isolation yield was 89%.

EXAMPLE 7

A reaction was conducted as described in Example 6 except that benzoic acid and PGE were replaced with 210 mmol of thiophenol and 100 mmol of 2,2-bis(4-glycidyloxyphenyl)propane, respectively. Desired 2,2-bis[4-(2-hydroxy-3-phenylpropyloxy)phenyl]propane was formed in an analytical yield of 94% and isolated in a yield of 90%.

EXAMPLE 8

A reaction was conducted as described in Example 6 except that benzoic acid and PGE were replaced with the same molar amounts of p-toluenesulfonic acid and styrene oxide, respectively. Products were 2-hydroxy-2-phenylethyl p-toluenesulfonate and 2-hydroxy-1-phenylethyl p-toluenesulfonate, both of which have the substructure (7), in a ratio of about 6:4. Total analytical and isolation yields of these products were 92% and 87%, respectively.

EXAMPLE 9

A reaction was conducted as described in Example 6 except that benzoic acid was replaced with 105 mmol of 2,2-bis(4-hydroxyphenyl)propane and the amount of PGE was 200 mmol. Desired 2,2-bis[4-(2-hydroxy-3-phenoxypropyloxy)phenyl]propane was formed in analytical yield of 94% and isolated in a yield of 89%.

EXAMPLE 10

A reaction was conducted as described in Example 6 except that benzoic acid and PGE were replaced with the same molar amounts of 4-methoxyphenol and 1,2-epoxy-4,5-dimethoxycyclohexane. Desired 2-(4-methoxyphenoxy)-4,5-dimethoxycyclohexanol was formed in analytical yield of 96% and isolated in a yield of 92%.

EXAMPLE 11

A reaction was conducted as described in Example 6 except that benzoic acid was replaced with 105 mmol of 2,2-bis(4-hydroxyphenyl)-1,1,1,3,3,3-hexafluoropropane and the amount of PGE was 200 mmol. Desired 2,2-bis[4-(2-hydroxy-3-phenoxypropyloxy)phenyl[-1,1,1,3,3,3-hexafluoropropane was formed in analytical yield of 89% and isolated in a yield of 83%.

EXAMPLE 12

A reaction was conducted as described in Example 6 except that benzoic acid was replaced with the same molar amount of acetic acid. Desired 2-hydroxy-3-phenoxypropyl acetate was formed in analytical yield of 98% and isolated in a yield of 94%.

EXAMPLE 13

A reaction was conducted as described in Example 6 except that benzoic acid and PGE were replaced with the same molar amounts of methanesulfonic acid and 4-phenoxystyrene oxide, respectively. Products were 2-hydroxy-2-(4-phenoxyphenyl)ethyl methanesulfonate and 2-hydroxy-1-(4-phenoxyphenyl)ethyl methanesulfonate, both of which have the substructure (7), in a ratio of about 5:5. Total analytical and isolation yields of these products were 96% and 92%, respectively.

EXAMPLE 14

A reaction was conducted as described in Example 6 except that benzoic acid was replaced with the same molar amount of 2-methoxyethyl benzoate, a compound represented by formula (3) where R$^2$ is phenyl and OZ$^1$ is an organic group derived from 2-methoxyethanol, and PGE was replaced with the same molar amount of 4-chlorophenyl glycidyl ether. Desired 1-(4-chlorophenoxymethyl)-2-(2-methoxyethoxy)ethyl benzoate was formed in an analytical yield of 93% and isolated in a yield of 86%.

EXAMPLE 15

A reaction was conducted as described in Example 6 except that benzoic acid was replaced with the same molar amount of acetic anhydride, a compound represented by formula (4) where R$^2$ is methyl and OZ$^2$ is an organic group derived from acetic acid. Desired 2,3-diacetoxypropyl phenyl ether was formed in an analytical yield of 90% and isolated in a yield of 86%.

EXAMPLE 16

A reaction was conducted as described in Example 6 except that benzoic acid was replaced with the same molar amount of diphenyl carbonate, a compound represented by formula (6) where R$^3$ is phenyl and OZ$^1$ is an organic group derived from phenol. Desired phenyl 1,3-diphenoxy-2-propyl carbonate was formed in an analytical yield of 89% and isolated in a yield of 81%.

EXAMPLE 17

A reaction was conducted as described in Example 6 except that benzoic acid was replaced with the same molar amount of methyl p-chlorophenyl carbonate, a compound represented by formula (6) where R$^3$ is methyl and OZ$^1$ is an organic group derived from p-chlorophenol. Only methyl 1-phenoxy-3-(p-chlorophenoxy)-2-propyl carbonate having the substructure (11) was formed in an analytical yield of 95% and isolated in a yield of 83%.

EXAMPLE 18

A reaction was conducted as described in Example 6 except that benzoic acid was replaced with the same molar amount of methyl 2-methoxyethyl carbonate, a compound represented by formula (6) where $R^3$ is methyl and $OZ^1$ is an organic group derived from 2-methoxyethanol. Products were methyl 1-phenoxy-3-(2-methoxyethoxy)-2-propyl carbonate having the substructure (11) and 2-methoxyethyl 3-methoxy-1-phenoxy-2-propyl carbonate having the substructure (12), in a ratio of about 1:1. The total analytical and isolation yields of these products were 97% and 93%, respectively.

EXAMPLE 19

A reaction was conducted as described in Example 6 except that benzoic acid was replaced with the same molar amount of methyl ethyl carbonate, a compound represented by formula (6) where $R^3$ is methyl and $OZ^1$ is an organic group derived from ethanol. Products were methyl 1-phenoxy-3-ethoxy-2-propyl carbonate having the substructure (11) and ethyl 3-methoxy-1-phenoxy-2-propyl carbonate having the substructure (12), in a ratio of about 1:1. The total analytical and isolation yields of these products were 93% and 88%, respectively.

EXAMPLE 20

A reaction was conducted as described in Example 6 except that benzoic acid was replaced with the same molar amount of benzoic anhydride, a compound represented by formula (4) where $R^2$ is phenyl and $OZ^2$ is an organic group derived from benzoic acid. Desired 1,2-dibenzoyloxy-3-phenoxypropane was formed in an analytical yield of 98% and isolated in a yield of 94%.

EXAMPLE 21

A reaction was conducted as described in Example 6 except that benzoic acid was replaced with the same molar amount of 2-naphthyl p-toluenesulfonate, a compound represented by formula (5) where $R^2$ is p-tolyl and $OZ^1$ is an organic group derived from 2-naphthol. Desired 1-(2-naphthyloxy)-3-phenoxy-2-propyl p-toluenesulfonate was formed in an analytical yield of 96% and isolated in a yield of 92%.

EXAMPLE 22

A reaction was conducted as described in Example 6 except that benzoic acid was replaced with the same molar amount of 4-chlorophenyl methacrylate, a compound represented by formula (3) where $R^2$ is isopropenyl and $OZ^1$ is an organic group derived from 4-chlorophenol. Desired 1-(4-chlorophenoxy)-3-phenoxy-2-propyl methacrylate was formed in an analytical yield of 96% and isolated in a yield of 90%.

EXAMPLE 23

A reaction was conducted as described in Example 6 except that benzoic acid was replaced with the same molar amount of methacrylic anhydride, a compound represented by formula (4) where $R^2$ is isopropenyl and $OZ^2$ is an organic group derived from methacrylic acid. Desired 2,3-bis(isopropenylcarbonyloxy)propyl phenyl ether was formed in an analytical yield of 91% and isolated in a yield of 89%.

EXAMPLE 24

A reaction was conducted as described in Example 6 except that benzoic acid was replaced with the same molar amount of methyl propanesulfonate, a compound represented by formula (5) where $R^2$ is propyl and $OZ^1$ is an organic group derived from methanol. Desired 1-methoxy-3-phenoxy-2-propyl propanesulfonate was formed in an analytical yield of 94% and isolated in a yield of 91%.

EXAMPLE 25

A reaction was conducted as described in Example 6 except that benzoic acid was replaced with the same molar amount of 4-trifluoromethylphenyl ethylenesulfonate, a compound represented by formula (5) where $R^2$ is vinyl and $OZ^1$ is an organic group derived from 4-trifluoromethylphenol. Desired 1-phenoxy-3-(4-trifluoromethyl)phenoxy-2-propyl ethylenesulfonate was formed in an analytical yield of 89% and isolated in a yield of 86%.

EXAMPLE 26

A reaction was conducted as described in Example 6 except that benzoic acid was replaced with the same molar amount of 3-benzyloxypropyl methanesulfonate, a compound represented by formula (5) where $R^2$ is methyl and $OZ^1$ is an organic group derived from 3-benzyloxypropanol. Desired 1-(3-benzyloxy)propoxy-3-phenoxy-2-propyl methanesulfonate was formed in an analytical yield of 97% and isolated in a yield of 92%.

EXAMPLE 27

Precisely weighed were 54.7 g of octanol (420 mmol) and 0.585 g of partially hydrated tris[tris(dimethylamino)phosphoranylidene-amino]phosphine oxide, $[(Me_2N)_3P=N]_3P=O.0.29H_2O$, (1.0 mmol) and these were placed in a 200 mL autoclave. After warming to 80° C., the mixture was reacted for 15 hours while intermittently supplying 23.2 g of propylene oxide (400 mmol), maintaining a reaction pressure of 0.3 MPa (absolute pressure). The mixture was cooled to room temperature over about 30 min. A small portion of the mixture was taken to be subject to quantitative analysis by gas chromatography, indicating that desired 1-(2-hydroxypropoxy)octane was formed in an yield of 81%. The reaction solution was purified by column chromatography to give 61.8 g of 1-(2-hydroxypropoxy)octane. An isolation yield was 78%.

EXAMPLE 28

A reaction was conducted as described in Example 27 except that octanol was replaced with the same molar amount of octyl acetate, a compound represented by formula (3) where $R^2$ is methyl and $OZ^1$ is an organic group derived from octanol, and a reaction temperature was 90° C. Desired 2-octyloxy-1-methylethyl acetate was formed in an analytical yield of 76% and isolated in a yield of 69%.

EXAMPLE 29

A reaction was conducted as described in Example 27 except that octanol was replaced with the same molar amount of diethylene glycol and the amount of propylene oxide was 800 mmol. Desired di-2-(2-hydroxypropyloxy) ethyl ether was formed in an analytical yield of 85% and isolated in a yield of 74%.

EXAMPLE 30

A reaction was conducted as described in Example 27 except that octanol was replaced with the same molar amount of di-2-mercaptoethyl ether and the amount of propylene oxide was 800 mmol. Desired di-2-(2-hydroxypropylthio)ethyl ether was formed in an analytical yield of 72% and isolated in an yield of 68%.

EXAMPLE 31

A reaction was conducted as described in Example 6 except that benzoic acid was replaced with the same molar amount of diphenyl adipate, a compound represented by formula (3) where $R^2$ is 4-(phenoxycarbonyl)butyl and $OZ^1$ is an organic group derived from phenol, and the amount of PGE was doubled. Desired bis(1-phenoxymethyl-2-phenoxy)ethyl adipate was formed in an analytical yield of 92% and isolated in a yield of 90%.

EXAMPLE 32

A reaction was conducted as described in Example 6 except that benzoic acid was replaced with the same molar amount of dimethyl terephthalate, a compound represented by formula (3) where $R^2$ is 4-(methoxycarbonyl)phenyl and $OZ^1$ is an organic group derived from methanol, and the amount of PGE was doubled. Desired bis(1-phenoxymethyl-2-methoxy)ethyl terephthalate was formed in an analytical yield of 89% and isolated in a yield of 84%.

EXAMPLE 33

A reaction was conducted as described in Example 6 except that benzoic acid was replaced with the same molar amount of 1,4-bis(acetoxycarbonyl)benzene, a compound represented by formula (4) where $R^2$ is 4-(acetoxycarbonyl)phenyl and $OZ^2$ is an organic group derived from acetic acid, and the amount of PGE was doubled. Desired bis(1-phenoxymethyl-2-acetoxy)ethyl terephthalate was formed in an analytical yield of 98% and isolated in a yield of 94%.

TABLE 1

| Exam. No. | Catalyst | Reaction yield (%) | Catalyst activity (mol/mol/h) |
|---|---|---|---|
| Ex. 1 | $[(Me_2N)_3P=N]_3P=O$ | 96 | 20 |
| Ex. 2 | $[(Me_2N)_3P=N]_3P=O.0.29H_2O$ | 97 | 20 |
| Comp. Ex. 1 | None | 4 | — |
| Comp. Ex. 2 | $BF_3.OEt_2$ | 31 | 6.2 |
| Comp. Ex. 3 | NMI | 51 | 10 |
| Comp. Ex. 4 | TPP | 64 | 13 |

TABLE 2

| Exam. No. | Catalyst | Amount of cat.(molar ratio) (cat./PGE) | Reaction yield (%) | Cat. activity (mol/mol/h) |
|---|---|---|---|---|
| Ex.3 | $[(Me_2N)_3P=N]_3P=O.0.29H_2O$ | $1.0 \times 10^{-2}$ | 98 | 20 |
| Comp. Ex. 5 | None | — | 2 | — |
| Comp. Ex. 6 | NMI | $10.0 \times 10^{-2}$ | 66 | 1.3 |
| Comp. Ex. 7 | $n\text{-}Bu_4NCl$ | $2.5 \times 10^{-2}$ | 42 | 3.4 |
| Comp. Ex. 8 | t-BuOK | $2.5 \times 10^{-2}$ | 48 | 3.9 |

As described above, according to this invention, an epoxy compound can be reacted with an alcohol, thiol, phenol, thiophenol, carboxylic acid, sulfonic acid, carbonate, carboxylic anhydride, sulfonate or carbonate under milder conditions than those in a process of the prior art, to give a desired, corresponding oxyalkylene derivative in a high yield.

What is claimed is:

1. A process for preparing an oxyalkylene derivative, comprising, in the presence of a phosphine oxide represented by formula (1):

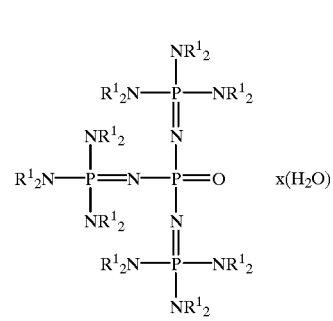

Formula (1)

where $R^1$ is the same or different and each represents a hydrogen or hydrocarbon group with 1 to 10 carbon atoms, and x is the amount of water as a molar ratio which is 0 to 5.0, reacting an epoxy compound with i) an alcohol, thiol, phenol, thiophenol, carboxylic acid or sulfonic acid represented by formula 2:

$$H\text{—}Q \qquad \text{Formula(2)}$$

where H is an active hydrogen and Q is an organic moiety of the alcohol, thiol, phenol, thiophenol, carboxylic acid or sulfonic acid except the active hydrogen;

ii) a carboxylate represented by formula (3), a carboxylic anhydride represented by formula (4) or a sulfonate represented by formula (5):

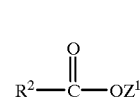

Formula (3)

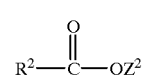

Formula (4)

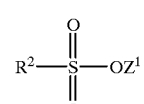

Formula (5)

where in formulas (3), (4) and (5) $R^2$ is hydrogen or an organic group having 1 to 35 carbon atoms; in formulas (3) and (5) $OZ^1$ is an organic moiety of the alcohol or phenol except the active hydrogen; and in formula (4) $OZ^2$ is an organic moiety of the carboxylic acid except the active hydrogen; or iii) a carbonate represented by formula (6)

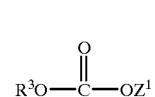

Formula (6)

where $R^3$ is aliphatic hydrocarbon group having 1 to 35 carbon atoms or aromatic hydrocarbon group having 6 to 35 carbon atoms, and $OZ^1$ is as defined above for formula (3) and (5), to form respectively an oxyalkylene derivative having i) a substructure represented by formula (7):

Formula (7)

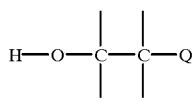

ii) a substructure represented by formula (8), (9) or (10):

Formula (8)

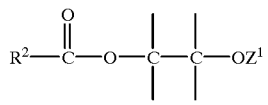

Formula (9)

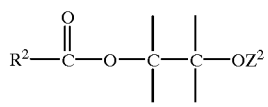

Formula (10)

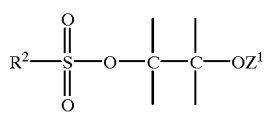

or iii) a substructure represented by formula (11) and/or a substructure represented by formula (12):

Formula (11)

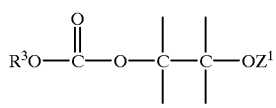

Formula (12)

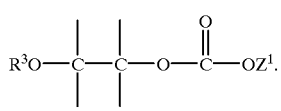

2. A process as claimed in claim 1, where in the phosphine oxide represented by formula (1), $R^1$ is the same or different and each represents a aliphatic hydrocarbon group having 1 to 8 carbon atoms.

3. A process as claimed in claim 1, where in the phosphine oxide represented by formula (1), $R^1$ is the same or different and each represents methyl or ethyl.

4. A process as claimed in claim 1, where in the phosphine oxide represented by formula (1), x is 0 to 2.0.

5. A process as claimed in claim 1, where the epoxy compound is selected from aliphatic, alicyclic or aromatic epoxy compounds consisting of carbon and hydrogen atoms and an oxygen of the epoxy group; and aliphatic, alicyclic or aromatic epoxy compounds having an ether bond.

6. A process as claimed in claim 1, where the alcohol represented by formula (2) is selected from aliphatic alcohols consisting of carbon and hydrogen atoms and an oxygen atom of the alcoholic hydroxyl group; and aliphatic alcohols having an ether bond.

7. A process as claimed in claim 1, where the thiol represented by formula (2) is selected from aliphatic thiols consisting of carbon and hydrogen atoms and a sulfur atom of the thiol mercapto group; and aliphatic thiols having an ether bond.

8. A process as claimed in claim 1, where the phenol represented by formula (2) is selected from phenols consisting of carbon and hydrogen atoms and an oxygen atom of the phenolic hydroxyl group; halogenated phenols; and phenols having an ether bond.

9. A process as claimed in claim 1, where the thiophenol represented by formula (2) is selected from thiophenols consisting of carbon and hydrogen atoms and a sulfur atom of the thiophenol mercapto group.

10. A process as claimed in claim 1, where the carboxylic acid represented by formula (2) is selected from aliphatic and aromatic carboxylic acids consisting of carbon and hydrogen atoms and an oxygen atom of the carboxyl group.

11. A process as claimed in claim 1, where the sulfonic acid represented by formula (2) is selected from aliphatic and aromatic sulfonic acids consisting of carbon and hydrogen atoms, a sulfur atom in the sulfonic group and an oxygen atom of the sulfonic group.

12. A process as claimed in claim 1, where $R^2$ in the carboxylate represented by formula (3), the carboxylic anhydride represented by formula (4) and the sulfonate represented by formula (5) is selected from an alkyl group having 1 to 35 carbon atoms; an alkenyl group having 2 to 35 carbon atoms; an aryl group having 6 to 35 carbon atoms; an aliphatic hydrocarbon group having 3 to 35 carbon atoms and at least one carboxylate group; an aromatic hydrocarbon group having 8 to 35 carbon atoms and at least one carboxylate group; and an aromatic hydrocarbon group having 8 to 35 carbon atoms and at least one carboxylic anhydride group.

13. A process as claimed in claim 1, where $OZ^1$ in the carboxylate represented by formula (3) and the sulfonate represented by formula (5) is an organic group derived from an aliphatic alcohol consisting of carbon and hydrogen atoms and an oxygen atom of an alcoholic hydroxyl group; an aliphatic alcohol having an ether bond; a phenol consisting of carbon and hydrogen atoms and an oxygen atom of a phenolic hydroxyl group; or a halogenated phenol.

14. A process as claimed in claim 1, where $OZ^2$ in the carboxylic anhydride represented by formula (4) is an organic group derived from an aliphatic or aromatic carboxylic acid consisting of carbon and hydrogen atoms and an oxygen of a carboxyl group.

15. A process as claimed in claim 1, where $R^3$ in the carbonate group represented by formula (6) is an alkyl group having 1 to 35 carbon atoms or an aromatic hydrocarbon group having 6 to 12 carbon atoms.

16. A process as claimed in claim 1, where $OZ^1$ in the carbonate represented by formula (6) is an organic group derived from an aliphatic alcohol consisting of carbon and hydrogen atoms and an oxygen atom of an alcoholic hydroxyl group; an aliphatic alcohol having an ether bond; a phenol consisting of carbon and hydrogen atoms and an oxygen atom of a phenolic hydroxyl group; or a halogenated phenol.

17. A process as claimed in claim 1, where in the carboxylate represented by formula (3), $R^2$ is an alkyl group having 1 to 6 carbon atoms, an alkenyl group having 2 to 4 carbon atoms, an aryl group having 6 to 10 carbon atoms, an aliphatic hydrocarbon group having 3 to 13 carbon atoms and at least one carboxylate group, or an aromatic hydrocarbon group having 8 to 16 carbon atoms and at least one carboxylate group; and $OZ^1$ is an organic group derived from an aliphatic alcohol having 1 to 20 carbon atoms consisting of carbon and hydrogen atoms and an oxygen atom of an alcoholic hydroxyl group or a phenol having 6 to 27 carbon atoms consisting of carbon and hydrogen atoms and an oxygen atom of a phenolic hydroxyl group.

* * * * *